United States Patent [19]

Hanna et al.

[11] Patent Number: 5,266,723
[45] Date of Patent: Nov. 30, 1993

[54] PROCESS FOR THE PREPARATION OF OPTICALLY ACTIVE 2-ARYL-ALKANOIC ACIDS, ESPECIALLY 2-ARYL-PROPIONIC ACIDS

[75] Inventors: Samir B. Hanna, Rolla, Mo.; Bernd Schneider; Henrich H. Paradies, both of Iserlohn, Fed. Rep. of Germany

[73] Assignee: Medice, Ltd., Chem.-Pharm. Fabrik Putter GmbH & Co. KG, Iserlohn, Fed. Rep. of Germany

[21] Appl. No.: 486,979

[22] Filed: Feb. 27, 1990

Related U.S. Application Data

[63] Continuation-in-part of Ser. No. 352,269, May 16, 1989.

[51] Int. Cl.$^5$ .................. C07L 59/48; C07L 63/36
[52] U.S. Cl. .................................................. 562/490
[58] Field of Search .................. 568/814; 570/201; 562/470, 490, 496

[56] References Cited

U.S. PATENT DOCUMENTS

| | | | |
|---|---|---|---|
| 3,686,183 | 8/1972 | Dyson | 562/490 |
| 3,877,926 | 4/1975 | Martin | 570/201 |
| 4,164,415 | 8/1979 | Kamesaran | 562/490 |
| 4,209,638 | 6/1982 | Nicholson et al. | 562/401 |
| 4,579,968 | 4/1986 | Castaldi et al. | 562/490 |
| 4,605,758 | 8/1980 | Schloemer | 562/490 |
| 4,654,438 | 3/1987 | Schloemer | 562/490 |
| 4,675,418 | 6/1987 | Giordano | 562/490 |

FOREIGN PATENT DOCUMENTS

| | | |
|---|---|---|
| 158913 | 10/1985 | European Pat. Off. |
| 195717 | 9/1986 | European Pat. Off. |
| 205215 | 12/1986 | European Pat. Off. |
| 2404159 | 1/1973 | Fed. Rep. of Germany |
| 2019542 | 1/1987 | Japan |

OTHER PUBLICATIONS

Hutt, et al. J. Pharm. Pharmacol., 1983, 35, 693-704.
Blaschle, Angew., 1980 92, 14-25.
Piccilo, et al., J. Org. Chem., 1985, 50, 3945-3946.
(List continued on next page.)

*Primary Examiner*—Paul J. Killos
*Attorney, Agent, or Firm*—Scully, Scott, Murphy & Presser

[57] ABSTRACT

A chemical process is disclosed for the preparation of a pharmaceutically active compound in an enantiomeric form either (R) or (S) of the structure

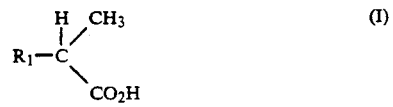 (I)

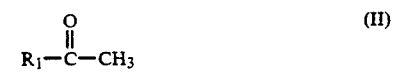

(II)

and a suitable pharmaceutical salt, e.g. alkali or earth metal, D-glucamine or D-ribamine, where $R_1$ represents an optionally substituted aryl group same as phenyl or naphthyl group, optionally including a heterocyclic ring system, which is optionally substituted, or represents a hetero-aromatic ring system optionally containing in addition to carbon atoms one or more atoms selected from the group consisting of nitrogen and oxygen; the enantiomeric R or S-compounds of (I) are obtained from a suitable ketone (II) by reduction with an $LiAlH_4^-$ "chiraldid-complex" to the corresponding S- or R-alcohol, following chlorination with retention of configuration, and producing a steriochemical pure R or S magnesium organic compound by subsequent carbonation with carbon dioxide in the presence of a ligand by keeping the stereochemical configuration R or S at 98% enantiomeric excess at least including high yields, and if desired converting compounds (I) into a pharmaceutically acceptable salt or ester thereof. Especially pharmaceutically complexes with D-glucamine and D-ribamine in a stoichiometric ratio of 1:1, including salts comprised of N-cationic detergents with 2-(S)-aryl-alkanoic acids.

66 Claims, 15 Drawing Sheets

OTHER PUBLICATIONS

Chemical Abstracts 1983 98:143138K.
Chemical Abstracts 1979 91:20125b.
Chemical Abstracts 1982 96:68650z.
Chemical Abstracts 1979 90:168303h.
Chemical Abstracts 1978, 89 239756.
Chemical Abstracts 1978 88:104920h.
Chemical Abstracts 1983 98:178945y.
Hayashi, et al. J. Org. Chem. 1983, 48, 2197–2202.
Rieu et al., Tetrahedron Report, 1986, 205, 4095–4131.
Noyori, et al., JACS, 1979, 101, 3129–3131.
Chemical Abstracts 88:50512f (1978).
Kobler, et al., Liebig's Ann. Chem. 1978, 1946–1962.
Foulkes and Hutton, Synthetic Communications, 1979, 9(7), 625–630.
Yamaguchi, et al., JACS, 1972, 94 (26), 9254–9255.
Larsen, et al., JACS, 1089, 111, 7650–7651.
Corey, et al., JACS, 1987, 109, 5551–5553.
Chemical Abstracts 198092: 62531.

REDUCTION WITH (−) 2,2'-Dihydroxy-1,1'-binaphthyl:

PROCESS FOR THE PREPARATION OF OPTICALLY ACTIVE 2-ARYL-ALKANOIC ACIDS, ESPECIALLY 2-ARYL-PROPIONIC ACIDS

This application is a continuation-in-part of our co-pending application Ser. No. 352,269, filed May 16, 1989, abandoned.

FIELD OF THE INVENTION

The present invention relates to a stereospecific chemical synthesis of optically pure enantiomers of 2-aryl-alkanoic acids, especially those of 2-aryl-propionic acids, in high chemical yields and large quantities. Starting from unsymmetrical ketones produced, e.g. by a Friedel-Crafts reaction, the stereospecific reduction to the S- or R-enantiomeric form, respectively, of the corresponding carbinol is achieved by a complexed reducing reagent consisting of lithium-aluminium-hydride and an optically pure diamino-alcohol, resulting in high chemical yields, where the enantiomer (R or S) has a high optical purity. The subsequent chemical steps in the chemical synthesis include halogenation by keeping the retention of the chiral configuration in an almost quantitative reaction.

BRIEF SUMMARY OF THE INVENTION

The present invention relates to a chemical process for preparing optically active 2-aryl-alkanoic acids especially 2-aryl-propionic acids in high chemical yields and >98% optical purity, including novel intermediates of excellent optical yield (>97% as determined by rotation and NMR- methods). In particular, this invention concerns a novel chemical process for the preparation of a stereoselective synthesis of a chiral alcohol, a chiral magnesium or a mercury organic compound comprising two main steps: a stereoselective halogenation of a chiral alcohol, followed by metallation or by a reaction with alkali cyanide, and subsequent conversion by retention of configuration to the carboxylic acid. This invention especially concerns an overall enantiomeric-selective chemical synthesis since it allows the production of both enantiomeric forms, R and S separately in high chemical yield and excellent optical purity, only by changing solvent, temperature or additions of the "chiraldid" complex, without racemization.

Three different routes can be pursued to obtain optically pure 2-aryl-alkanoic acids at high chemical yields:
  i) the halides can be metallated with magnesium or mercury and subsequently treated with carbon dioxide;
  ii) or by producing the corresponding nitriles by changing configuration of the chiral carbon atoms (R→S, or S→R) and subsequent hydrolysis to the 2-aryl-alkanoic acids;
  iii) or by treatment of the enantiomeric halides with sodium tetracarbonyl ferrate-II [$Na_2Fe(CO)_4$] in the presence of carbon monoxide (CO); and subsequent treatment with sodium hypochlorite (NaOCl) and acid hydrolysis or by treating with a halogen (e.g. $J_2$) in the presence of an alcohol to give the enantiomeric ester, or in the presence of $J_2$ and water to yield, respectively, the corresponding free carboxylic acid.

This chemical process yields high optically pure 2-aryl-alkanoic acids, especially of 2-aryl-propionic acids, at high chemical yields.

BACKGROUND OF THE INVENTION

In 1981, Shen (Shen T. Y., in: Wolff, M. F. (ed) *Burger's Medicinal Chemistry*, 4th edition, part III, Wiley, Interscience, New York, pp. 1205-1271) reviewed the medicinal aspects of the aryl-acetic acids and their 2-methyl analogues, especially the 2-aryl-propionic acids. In particular, it has been reported that the in vitro anti-inflammatory activity resides in the S-enantiomer which is an optically active enantiomer of the racemate (R,S)-2-aryl-propionic acid which is up to 150 times as active as its R-enantiomer as described by Adams et al. (S. Adams et al., *J. Pharm. Pharmacol.*, 28, 1976, 256; A. J. Hutt and J. Caldwell, *Chemical Pharmacokinetics* 9, 1984, 371). Moreover, the chiral inversion by the metabolism in man of 2-aryl-propionic acids of the R-(−) enantiomer to the biologically active S-(+) enantiomer, especially in case of ibuprofen (R,S)-2-(4-isobutyl-phenyl)-propionic acid), supports the pharmacologically active principle of the S-(+)-enantiomer which is also supported by the studies of the S-enantiomer of Naproxen (A. J. Hutt and J. Caldwell, *J. Pharm. Pharmacol.*, 35, 1983, 693-694). In addition, there is no metabolic chiral inversion to the corresponding R-(−)-enantiomer of the S-(+) form in man, although some stereochemical inversion has been observed in rats occasionally, possibly due to unknown stereochemical interations of the (S)-(+) and R-(−) enantiomers at the site of action.

Since the conversion of the R-(−)-2-aryl-propionic acids to the pharmacologically active S-(+)-enantiomer is a reaction of great medicinal impact, it is likely that certain benefits will be obtained by the use of the S-(+)-enantiomers of 2-aryl-alkanoic acids as compounds as opposed to the racemates. The use of the S-(+) enantiomers would permit reduction of the dose given, reduce the gastro-intestinal side effects, reduce the acute toxicity, remove variability in the rate and extent of inversion, and in addition will reduce any toxicity arising from non-specific reactions.

Therefore, there is need of a process capable of operating on an industrial scale in order to produce economically attractive yields of these S-(+) enantiomers of high optical purity >98%, by applying a stereospecific chemical method. Optically pure enantiomers of 2-aryl-alkanoic acids, especially 2-aryl-propionic-acids which are approved for pharmaceutical use as a pure, optically active stereoisomer, e.g. S-(+)-(6-methoxy-2-naphthyl)-propionic acid (Naproxen) or S-(+) ibuprofen, can be obtained by using conventional ways of racemic separation by applying optically active bases, e.g. 2-phenyl-ethyl-amine, N-methyl-glucamine, cinchonidine, brucine or D-(−)-threo-1-p-nitrophenyl-2-aminopropan-1,3-diol or through biochemical racemate separation (P. Cesti and P. Piccardi, Eur. Pat. Appl. EP 195,717; 1986, J. S. Nicholson, and J. G. Tantum, U.S. Pat. No. 4,209,638, 1980), or by high performance liquid chromatographic techniques (see G. Blaschke, *Angew. Chem.* 92, 14-25, 1980). However, these methods of applying optically active bases or enzymes (pig liver esterase) have the drawback common to all these processes of high material costs, manufacturing labor and equipment for the recovery and racemization of the undesired optical stereoisomer not counting the energy necessary for redistillation of the solvents, low yields of crystalline compounds of high optical purity from the mother liquors. Thus the elimination of these resolution steps can result in substantial savings in material costs, manufacturing, labor and equipment.

Methods for synthesizing racemic 2-aryl-alkanoic acids, especially 2-aryl-propionic acids and in particular to R, S-ibuprofen are well known, see, for example, Tanonaka, T., et al., DE 3523082 A1, (1986), who uses microorganisms; JP-PSEN 40-7491 (1965); 47-18105, (1972); JP-OS 50-4040, (1975); DE 2404159 (1974); DE 1443429 (1968) by J. S. Nicholson and S. S. Adams; DE 2614306 by Bruzzese, T., et al., (1976); DE 2605650 by Gay, A., (1976); DE 2545154 by Heusser, J., (1976); and DE 2404160 by Kogure, K., et al., (1974).

Surprisingly, only a few methods for a stereospecific chemical synthesis for 2-aryl-alkanoic acids, especially 2-aryl-propionic acids, are known. Piccolo et al. (*J. Org. Chem.* 50, 3945–3946, 1985) describe a stereospecific synthesis by the alkylation of benzene or isobutylbenzene with (S)-methyl-2-[(chlorosulfonyl)-oxy] or 2-(mesyloxy) propionate in the presence of aluminium chloride yielding (S)-methyl-2-phenyl-propionate in good chemical yield (50–80%) and excellent optical yield of >97% as determined by rotation through inversion of configuration at the attacking carbon atoms. The reaction conditions are very similar as described in some patents (Jpn. Kokai Tokkyo Koho 5808045; *Chem. Abstracts,* 1983, 98; 14313 k; Jpn. Kokai Tokkyo Koho 7979246; *Chem. Abstracts,* 1980, 92, 6253 f) where racemic reagents have been used. Extensions of this type of reactions to other aromatic substrates, e.g. toluene, isobutylbenzene, tetraline, anisole, naphthalene, 2-methoxy-naphthalene are described in Jpn. Kokai Tokkyo Koho 7971932; *Chem. Abstracts* 1979, 91, 20125 b; Jpn. Kokai Tokkyo Koho 78128327; *Chem. Abstracts* 1978, 89, 23975 y; Jpn. Kokai Tokkyo Koho 81145241; *Chem. Abstracts* 1982, 96, 68650 z; Jpn. Kokai Tokkyo Koho 78149945; *Chem. Abstracts* 1979, 90, 168303 h; Jpn. Kokai Tokkyo Koho 7844537; *Chem. Abstracts* 1978, 89, 108693 h; Jpn. Kokai Tokkyo Koho 77131551; *Chem. Abstracts* 1978, 88, 104920 h. In a recent paper Piccolo et al. (*J. Org. Chem* 52, 10, 1987) describe a synthesis leading to R-(−) ibuprofen, whereas Tsuchihashi et al. (Eur. Pat. Appl. EP 67,698, (1982); *Chem. Abstracts* 98, 178945 y, (1983) report a stereospecific synthesis of the R-(−) ibuprofen- methylester with excellent yields of about 75.0% and high optical purity (>95%) in contrast to Piccolo et al. (*J. Org. Chem.* 32, 10, 1987) having an optical purity of 15% only for the R-(−) ibuprofen. However, the same authors have reported chemical yields of 68% of S-(+) ibuprofen having an optical purity of 75–78%, only. Hayashi, et al. (*J. Org. Chem.* 48, 2195, 1983; in: *Asymmetric Reactions and Processes In Chemistry;* eds E. L. Eliel and S. Otsuka, ACS-Symposium Ser. 1985, 1982, 177) describe a stereospecific synthesis of S-(+) ibuprofen through asymmetric Grignard cross-coupling which are catalyzed by chiral phosphine-nickel and phosphine- palladium complexes. The enantiomeric excess of the coupling products with various alkenyl halides under the influence of the above-mentioned metal phosphine complexes, including amino acids, depends strongly on the ligand and ranges up to 94% with enantiomeric excesses in the 60–70% range. A very useful ligand has been found in chiral 2-aminoalkyl phosphines achieving reasonable chemical yields and high optical purity. Furthermore, optically active 2-aryl-alkonates have been synthesized via a Friedel-Crafts synthesis by Sato and Murai (Jpn. Kokai Tokkyo Koho JP 61,210,049 t 86,210,049, 1986) yielding 46% S-(+) ibuprofen. Giordano et al. (EP application 0 158 913, 1985) has reported a process for the preparation of optically active 2-aryl-alkanoic acids and intermediates thereof by halogenation on the aliphatic carbon atom to the ketal group and rearrangements of the haloketals yielding pharmacologically active 2-aryl-alkanoic acids. A stereochemical synthesis of 2-aryl-propionic acids is described by Robertson et al. (EP application 0 205 215 A2, 1986) using 2-($R_1$)-alkane as the carbon source for the fungi Cordyceps in particular for *Cordiceps militaris,* yielding enantiomeric S-(+) products of high optical purity.

Methods for the synthesis of anti-inflammatory 2-aryl-propionic acids are listed in the review by Rieu et al. (J. P. Rieu, A. Boucherle, H. Coussee and G. Mouzin, *Tetrahedron Report* No. 205, 4095–4131, 1986), also. However, this report is mostly concerned with the racemates rather than an evaluation of stereospecific chemical synthesis of 2-aryl- propionic acids.

DETAILED DESCRIPTION OF THE INVENTION

This invention describes the stereospecific synthesis of the S- or R-enantiomers of 2-aryl-alkanoic acids, particularly 2-aryl-propionic acids, which can be applied easily in chemical plants. The advantage of this process is the use of simple available and economical chemicals, e.g. ketones, and asymmetric reduction with chiral reagents from lithium aluminum hydride complexes with (2S, 3R)-4-dimethylamino-3- methyl-1,2-diphenyl-2-butanol or 2,2'-dihydroxy-1,1'-binaphthyl [which can be re-used after the reaction], thionyl-chloride (bromide), magnesium or cyanide in conjunction with sodium- carbonyl-ferrate ($Na_2Fe(CO)_4$, Collman's reagent) in order to produce economical yields of S-(+) or R-(−)-2-aryl-alkanoic acids, preferably S-(+)-ibuprofen and S-(+) naproxen, of high optical purity (>98%).

The 2-aryl-alkanoic acids prepared according to the present invention fall within the chemical formula:

in which R is lower alkyl, Ar is preferably a monocyclic, polycyclic or ortho-condensed polycyclic aromatic group having up to twelve carbons in the aromatic system, e.g. phenyl, diphenyl, and naphthyl. The substituents on these aromatic ring systems comprise one or more halogen atoms, $C_1$–$C_4$ alkyls benzyl, hydroxy, $C_1$–$C_2$ alkoxy, phenoxy and benzoyl groups. Examples of such substituted aryls are: 4-isobutyl-phenyl, 3-phenoxy-phenyl, 2-fluoro-4-diphenyl, 4'-fluoro-4-diphenyl, 6-methoxy-2-naphthyl, 5-chloro-6-methoxy-2-naphthyl and 5-bromo-6-methoxy-naphthyl, 4-chlorophenyl, 4-difluoro-methoxy-phenyl, 6-hydroxy-2-naphthyl, and 5-bromo-6-hydroxy-2-naphthyl.

For reasons of clarity we define the meaning of the following terms and expressions used throughout this invention as follows:

Chiral refers to a chemical structure which has an asymmetric center, at least. The configuration of the asymmetric carbon atom is classified as "R" or "S" in accordance with the Cahn-Ingold-Prelog rules. Enantiomer or enantiomorph defines a molecule which is non-superimposable on its respective mirror image.

Enantiomeric excess, "e.e", refers to a definition which means percentage of the predominant enantiomer subtracted from the other enantiomer.

The ketones of the chemical formula (II) below are well known and are easily prepared by known methods through Friedel-Crafts acylation if not commercially available.

The stereospecific reduction to the corresponding S-(+)-1-(4-isobutylphenyl)-hydroxyethane (III) is accomplished by reacting the unsymmetrical ketone (II) with LiAlH$_4$ in complex with (+)-4-dimethylamino-3-methyl-1,2- diphenyl-2-butanol in etheral (or THF) solutions. Due to different conditions e.g. temperature, adding the reducing reagents, reaction time, by applying this particular reaction one can obtain easily the S-2-(4-isobutylphenyl)-2-hydroxy- ethane or the corresponding R-enantiomer in good chemical yields (almost 100% in chemical yield) and high optical purity (>95%).

Figure 1:
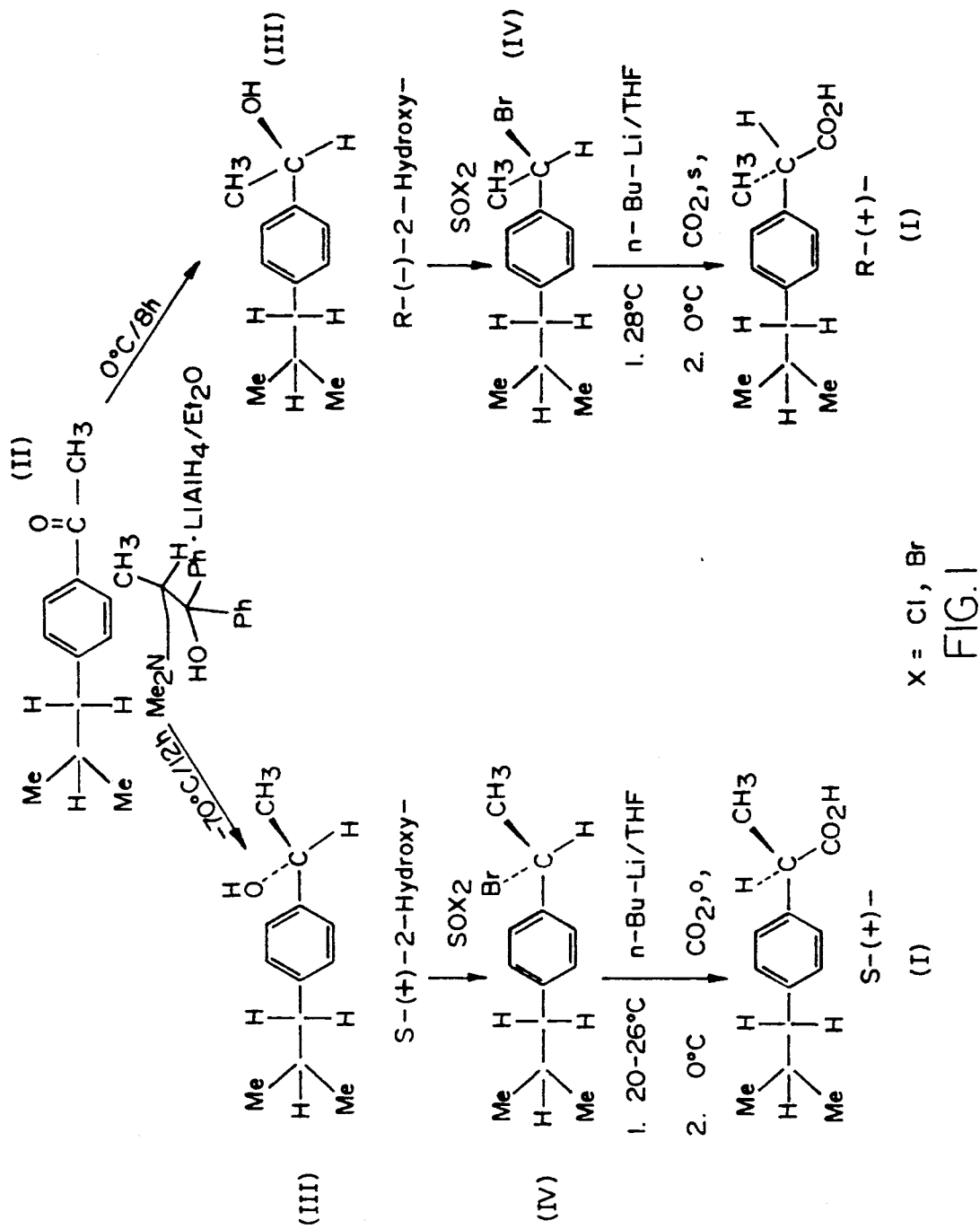
Figure 2:
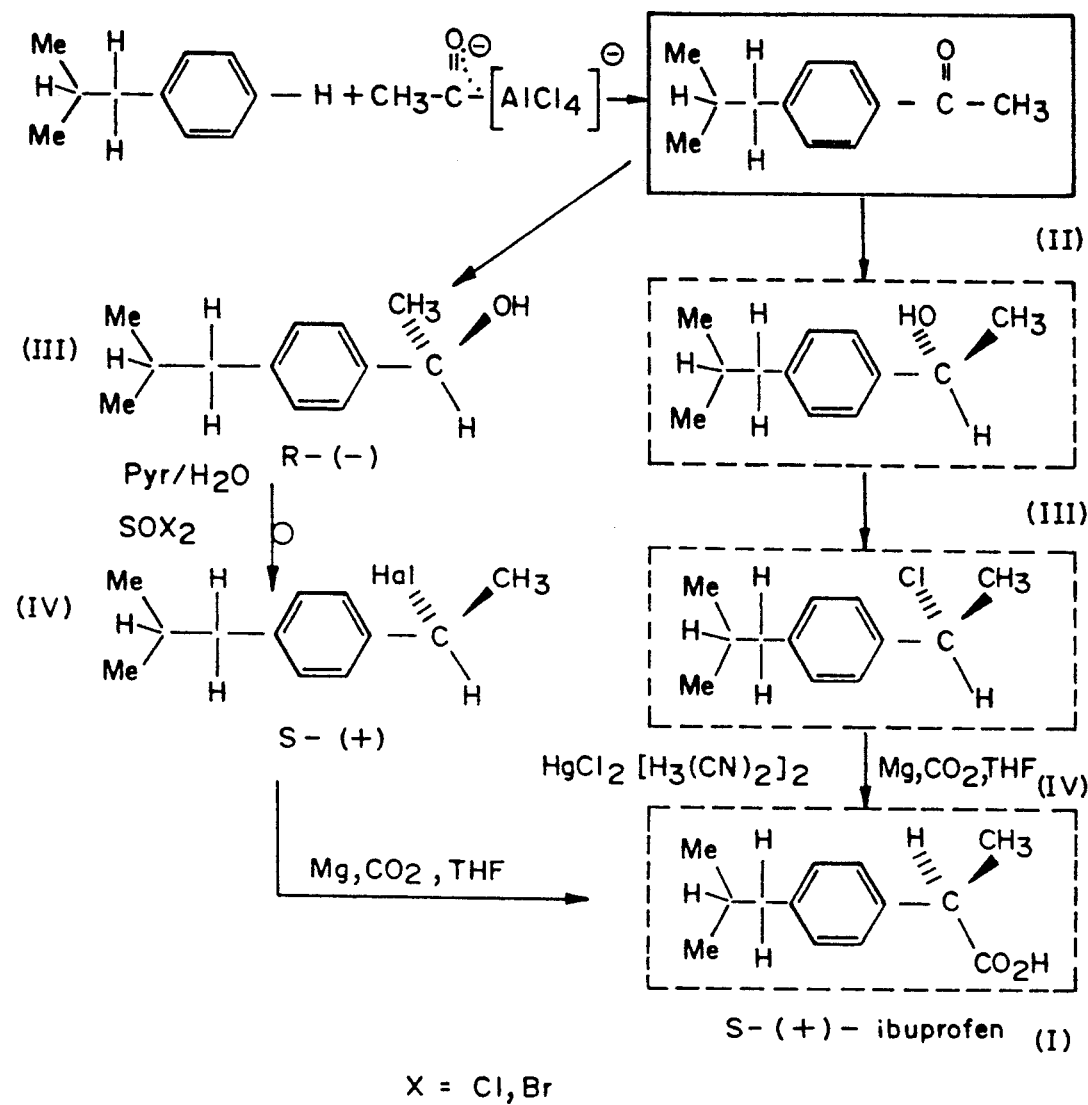
Figure 3:
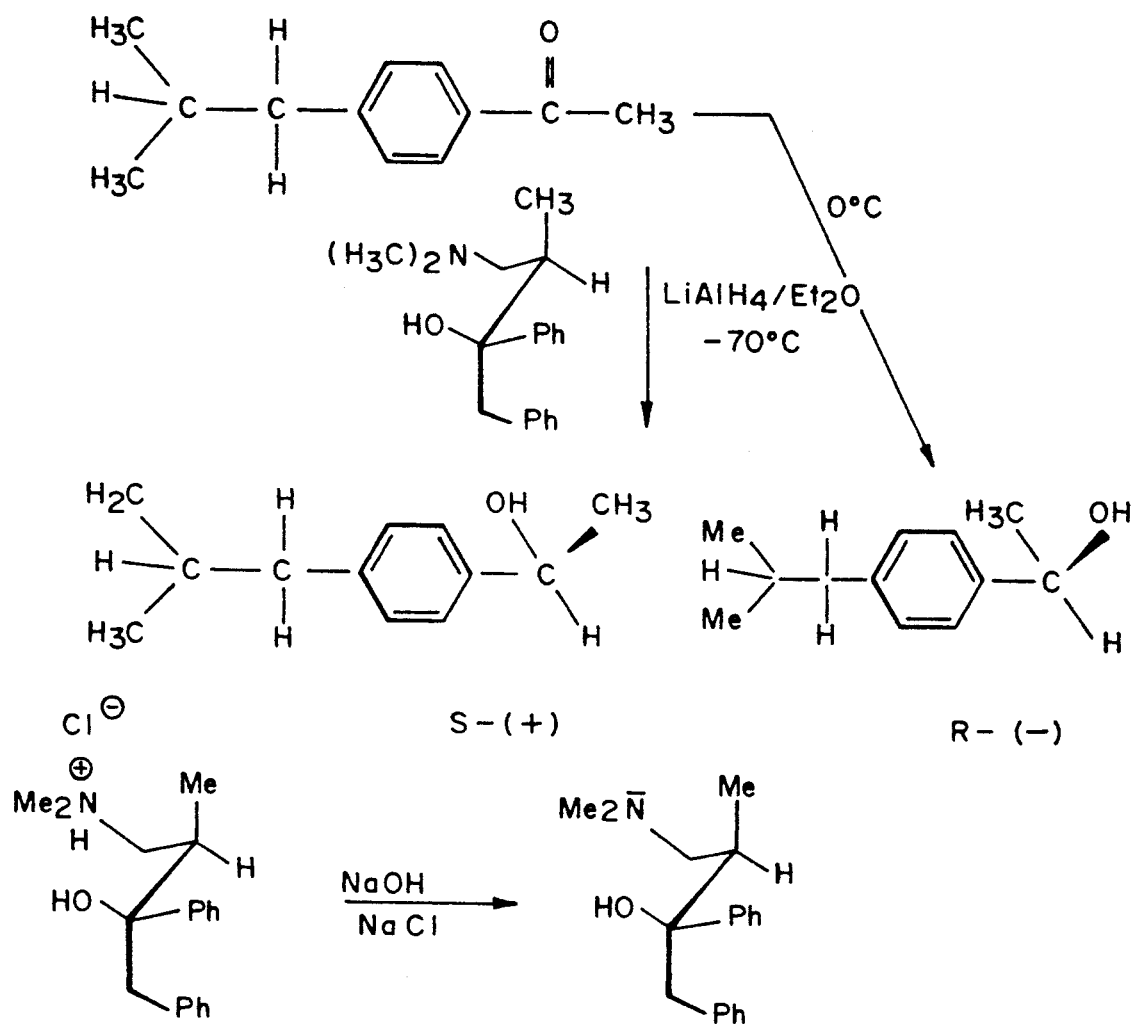

A schematic route for this particular synthesis of the S- or R-enantiomer is shown in FIG. 1 below, whereas FIGS. 2 and 3 show the procedure for obtaining S-(+) or R(−)-ibuprofen. This route (FIG. 2) stands for a general route to obtain pure enantiomers of 2-aryl-propionic acids, useful for industrial processes.

The asymmetric reduction with lithium aluminium hydride (LiAlH$_4$) in complex with (+)-(2S, 3R)-4-dimethylamino-3- methyl-1,2-diphenyl-2-butanol (S. Yamaguchi and H. S. Mosher, J. Org. Chem. 38, 1870, 1973) of the ketone (II) gives either (R)-(−) or (S)-(+)-1-(4-isobutylphenyl)-hydroxyethane in 98-99% enantiomeric purity depending upon use of this reagent either immediately after its preparation or upon aging overnight or refluxing for a few minutes. This particular reversal in stereoselectivity with age of the complexing reagent ("chiraldid reagent") can be used to provide 2-substituted-2-hydroxyethane derivatives having high optical purity and very good chemical yields of about 95% and more. These chemical yields with high optical purity can be obtained particularly from different carbonyl substrates of the formula (I′).

wherein Ar = 4-isobutylphenyl
= 6-methoxy-2-naphthyl
= 3-phenoxy-phenyl
= 2′fluoro-4-diphenyl
= 4′-fluoro-4-diphenyl
= 5-chloro-6-methoxy-2-naphthyl
= 5-bromo-6-methoxy-2-naphthyl
= 4-chloro-phenyl
= 4-difluoro-methoxy-phenyl
= 6-hydroxy-2-naphthyl
= 5-bromo-6-hydroxy-2-naphthyl The extent of stereoselectivity is determined by NMR methods by treating the carbinol obtained with excess acid chloride from (R)-(+)-2-methoxy-2-trifluoromethylphenylacetic acid in pyridine as described by J. A. Dale, D. C. Dull, and H. S. Mosher, J. Org. Chem. 34, 2543, (1969). The signals of both the 0-methyl and α-methyl groups of the R,R-diastereomer from methylphenylcarbinol appear at higher fields than those of the R, S-diastereomers. The peaks are clearly separated on a T-60 instrument and relative peak heights are shown to give a good approximation of the isomeric composition. Further, the $^{19}$F resonances for the 2 —CF$_3$ group at 94,1 MHz can be used also and readily integrated Applying a NMR shift reagent, e.g. Fn(fod)$_3$(0, 1M) can be used also to discriminate between the different R, R-diastereomers and R, S-diastereoisomers, respectively, so that quantitative integration of the respective 0-methyl signals is readily possible.

Another effective asymmetric reduction of prochiral carbonyl compounds according to the formula (II) with a hydride reagent containing a chiral auxiliary ligand can be achieved by using LiAlH$_4$ in complex with optically pure 2,2′-dihydroxy-1,1′-binaphthyl in the presence of a hydroxylic compound R′OH. The enantioselectivity is virtually complete (FIG. 4 below) in accordance with recent observations by Noyari et al. (R. Noyari, I. Tomino and Y. Tanimoto, J. Amer. Chem. Soc. 101, 3129-3130, 1979).

Since both R- and S-forms of the carbinols are readily accessible in optically pure forms, both methods allow the synthesis of both enantiomers of these carbinols from carbonyl compounds. Furthermore, the reduction of simple dialkyl ketones does not give satisfactory optical yields as these unsymmetric substituted ketones of formula II.

With respect to the reaction of LiAlH$_4$-(+)-4-dimethyl-amino-3-methyl-1,2-diphenyl-2-butanol with the ketones (II), it has been found that the optical yield increases by lowering the reaction temperature when using ether as a solvent. However, by applying tetrahydrofurane (THF) or 1,2-dimethoxy-ethane the reaction temperature is not crucial when the reaction conditions are below 30° C. In both cases the chemical yields are almost 95%.

The synthesis of R-(−) or the S-form from the ketone (II) including the subsequent transformations to the S- or R-enantiomer of the carboxylic acids, for obtaining high chemical yields, depends on the optical purity of the S- or R-enantiomers of the substituted 1-hydroxyethane. It has been found that the effects of temperature, concentration, solvent, time, ratio of the reactants, and velocity of stirring upon stereoselectivity of this reduction is of importance for obtaining high chemical yields (>90%) of the optically pure S- or R-enantiomeric forms.

Of foremost importance in the observed increase in chemical yield of the corresponding enantiomers (R or S) having high optical purity according to this reduction to the carbinol, is that the stereoselectivity is strongly dependent upon the length of time that the reagent, e.g. LiAlH$_4$R*OH (R*OH is (+)-(2S, 3R)-4-dimethylamino-3-methyl-1,2-diphenyl-2-butanol-2-butanol) has been permitted to stand before its use for reducing the ketone as a substrate. Accordingly, stirring velocity and time are important factors for producing the R- or S-enantiomeric forms in high chemical yield and optical purity, whereas the time parameter influences the stereoselectivity if R-(−) or S(−) is being produced from the carbonyl substrate. The stirring (mixing) in the absence of any oxygen and moisture determines mainly the chemical yield. According to this invention when, for example, 2-(4-isobutylphenyl)-methyl-ketone or 1-[4-2-methylpropyl]phenyl-ethanone [CAS Registry #38861-78-8] is added to the reagent, e.g. LiAlH$_4$ R*OH, at 4° C., (0° C.–4° C.) either 1 minute or 5 minutes after its preparation, an almost quantitative yield of R-(−)-2-(4-isobutyl-phenyl)-2-hydroxyethane is formed when continuously stirred. The preparation of the reducing agent is performed by mixing LiAlH₄R*OH with the ketone in a molar ratio of 1.0:2.5; normally a pasty cake is obtained in etheral solution at 0°-4° C. However, continuous stirring has to be provided in order to have an active reducing reagent.

The preparation of the reducing reagent, e.g. LiAlH₄ R*OH, in ethereal solution especially the colloidal state rather than the "caky" or suspended state influences the optical purity; the almost quantitative reduction of the carbonyl substrate which is governed by stirring the mixture of LiAlH₄R*OH and ketone, the colloidal state of the reducing reagent, LiAlH₄R*OH, rules the optical purity of the reagent which is nearly 95-98%.

However, when the reducing reagent is permitted to stand for eight hours or is refluxed in ether without stirring before the same carbonyl substrate is added, a 95-98% yield of the S-(+)-enantiomeric form of the carbinol, which is 95% optically pure, is obtained.

The observed reversal in stereoselectivity is associated with the colloidal state of LiAlH₄(R*OH)ₙ and the more soluble form of "LiAlH₄₋ₙ(R*OH)ₙ"+nH₂, still in colloidal state; however, more in a state of microemulsion. Stirring (continuous mixing) for a short period of time (time-scale minutes) is essential according to the reaction scheme:

$$LiAlH_4 + nR^*OH = LiAlH_{n-4}(OR^*) + nH_2$$

which can be measured by the evolution of hydrogen and forming a microemulsion rather than a precipitate. Practically, the constancy of the density of the state of the LiAlH₄₋ₙ(OR*) or the initial complex LiAlH₄₋ₙ-R*OH in ethereal or THF solutions is a reasonable assumption for the stereoselectivity, and any variation which is being applied to the colloidal system has effects on the chemical yields, rather than the optical purity. In accordance with this invention the successful preparation of the S-enantiomer of the carbinol from the corresponding ketone (II) as a substrate is preferred by allowing the reducing agent to stand for eight hours in ethereal or THF solutions at temperatures between −7° C.-0° C. before the corresponding ketone is added. The reduction is carried out and completed in 10-12 hours at 20° C. under continuous mixing.

The R-enantiomer of the carbinol from the corresponding ketone (II) is obtained preferably by forming the complex reducing agent, LiAlH₄₋ₙ(OR*)ₙ at 0° C. (down to −50° C.) and immediately adding (between 5-10 minutes) of the corresponding ketone in ethereal or THF solutions, followed by continuous stirring over a period of time of 8-12 hours at 20° C.

It has been found that the stereoselectivity of the reduction to the R-carbinol increases with decreasing temperature (−70° C. to 0° C.) by preparing the active reducing complex, whereas the stereoselectivity of the soluble active reducing reagent for the S-carbinol decreases with temperature. Reaction temperatures for forming the active reducing species, e.g. LiAlH₄₋ₙ(OR*)ₙ, and aging (time of standing of LiAlH₄₋ₙ(R*)ₙ) is important to stereoselectivity. However, the main density of the reaction mixture consisting of LiAlH₄₋ₙ(OR*)ₙ and the ketone with respect to the industrial process should be constant throughout the series of additions of the ketone. Thus, if the volumetric feed rate of the ketone with respect to the active reducing reagent is in the steady state, the rate of outflow from the reaction will be the same as the volumetric feed rate of the reacting ketone. So in terms of engineering design, it can be treated as a homogenous reaction mixture because there is complete mixing on a molecular scale with no particular residence time. If the feed consists of a suspension of colloidal particles, though there is a distribution of residence times among the individual particles, the mean residence time does correspond to the ratio of volume to volumetric feed rate, if the system is ideally stirred and mixed.

The reaction kinetics for conversion of the ketone to the corresponding enantiomeric carbinols can be enhanced by carrying out the reaction in the presence of 3A or 4A molecular sieves (zeolites) during the reaction. The advantages of using these sieves include, as discovered by applying this mechanism, economy, ease of isolation, increasing chemical yields including improving optical purities and enantiomeric excess, and the potential for in situ derivatization of the product. According to our invention with the stereospecific reduction of the ketones to the corresponding enantiomeric carbinols in the absence of (i) water, coming from incompletely dried reagents, solvents, equipment and moisture, (ii) diol ethers, generated by in situ during side reactions in the presence of water, (iii) hydroperoxides and (iv) improper colloidal state of the reducing chiral complex, are disadvantages in not using the molecular sieves during the reaction, causing decrease in chemical yields of optically pure corresponding carbinols.

It has been found that the highest stereoselectivities for both forms of the reactive reducing reagent, LiAlH₄₋ₙ (OR*)ₙ are obtained for ratios of LiAlH₄ to R*OH between 1.0:2.3 to 1.0:2.5 in accordance with Yamaguchi and Mosher (*J. Org. Chem.* 38, 1870, 1973), and does not appear to be critical for the processes described here. It has been found that the preparation of the active reducing agent, LiAlH₄₋ₙ (OR*)ₙ, in benzene, toluene, pentane and hexane instead of ether, THF, 1,2-dimethoxy-ethane, does not improve stereoselectivities over more polar solvents, e.g. ether, etc. However, nonpolar solvents are very useful for reducing ketones with the active reducing reagent when methoxy- or chloro, bromo, and fluoro substitutents are located in the aryl-groups since they are not affected in these solvents by the reducing reagent, hence high chemical yields with high optical purities are obtained. One advantage of using this chiral reducing reagent for preparing enantiomeric carbinols of high optical purity on a large scale basis is the recovery of the (+)-4-dimethylamino-3-methyl-1,2-diphenyl-2-butanol after reaction with hydrochloric acid and subsequent neutralization with sodium carbonate. So the optically active diamino alcohol can be re-used which makes this reducing step very economical at low costs, and almost quantitative yields.

Figure 4:
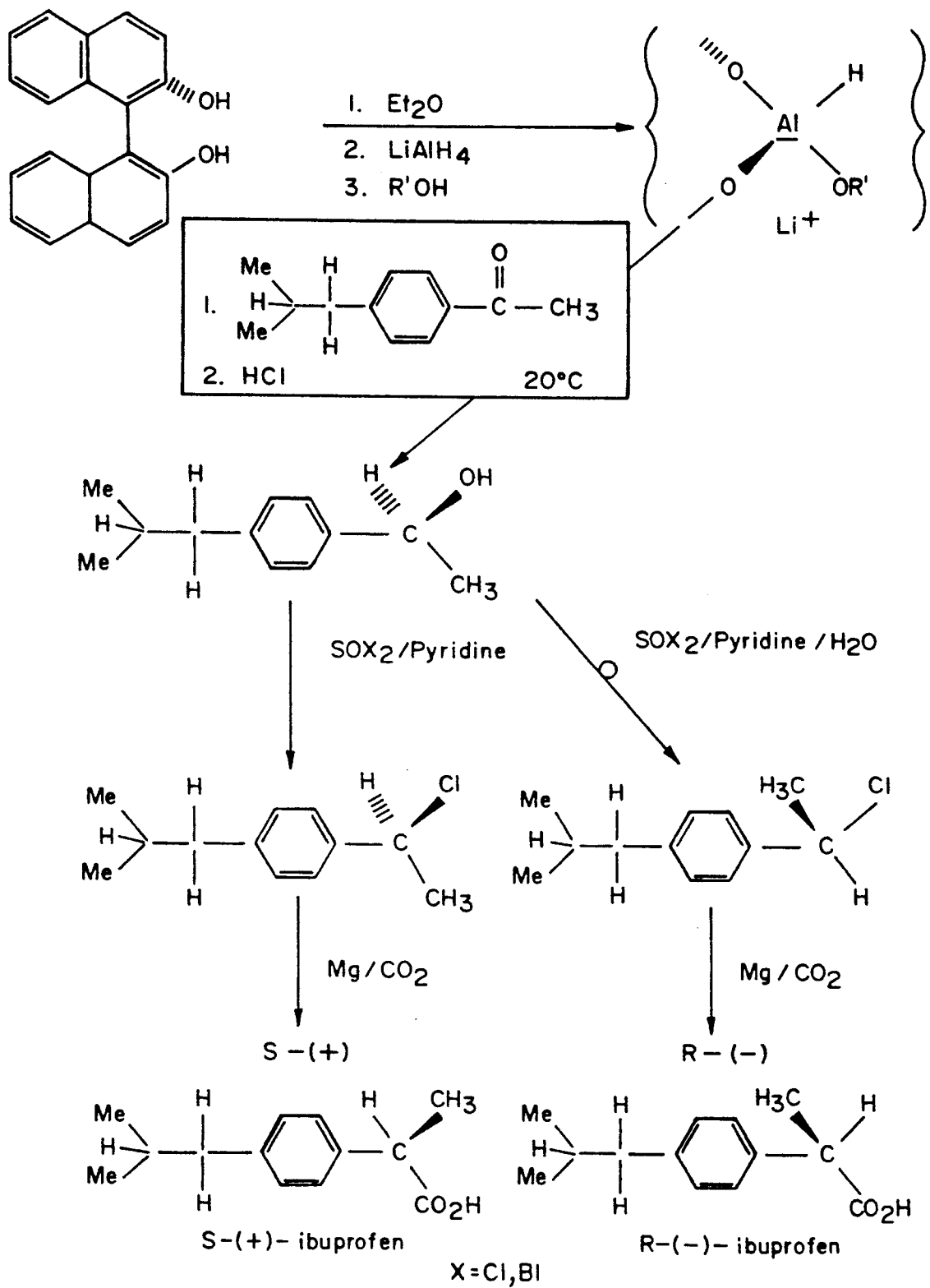

The same procedure can be applied by using 2,3'dihydroxy-1,1'binaphthyl as well as for the recovery of this particular reducing agent (FIG. 4 below).

Figure 5:
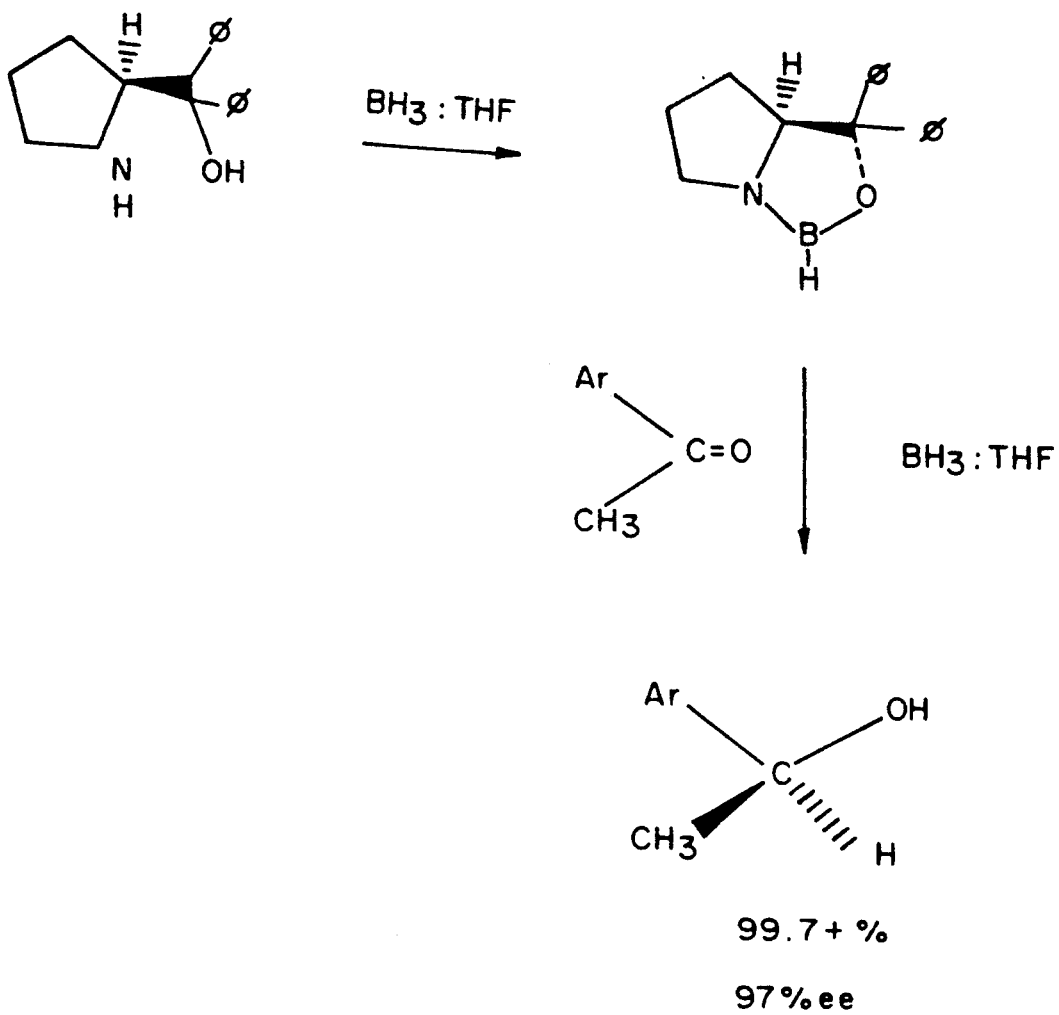

Another procedure which brings about the asymmetric reduction of ketones, e.g. II, employs a complex between boron hydride and tetra hydrofuran (BH₃:THF) and the chiral amino-alcohol, S-(−)-1,1-diphenyl-prolinol according to well-established methodoloy (Corey, Bakshi and Shibata, *J. Amer. Chem. Soc.* 109, 5551 (1987)). The yields are 99.7%, with 97% ee (FIG. 5).

Stereospecific halogenation of the enantiomeric carbinol, R or S, (III), by keeping retention of configuration of the chiral carbon can be performed either with thionylchloride or thionylbromide, or cyanuric chloride in high chemical yields (almost quantitative) and high optical purity. Preferably, the halogenation is performed in 1,4- dioxane, water-free, when using high amounts of the carbinols, whereas dry pyridine can be used also. The enantiomeric carbinols are normally dissolved in 1,4-dioxane at 20° C. by adding the stoichiometric amounts of thionylchloride dropwise under continuous mixing over a period of time of one hour. The reaction should continue in the case of thionylchloride or bromide for 30 minutes further. The excess of $SOCl_2$ or $SOBr_2$ is eliminated by passing a dry stream of nitrogen through the reaction solution at 20° C. for approximately five hours, unless the R- or S-enantiomeric chloride is being recovered through high vacuum distillation.

A typical procedure for preparation of the enantiomeric chloride involves heating of the enantiomeric carbinols with powdered cyanuric chloride (1 mol) to 10°–20° C. above the boiling point of the carbinols or in the presence of a base (0.5 mol $NaOCH_3$ or NaOBu). After the addition (ca. 1 -1,5 h), the reaction mixture is cooled, filtered and distilled under high vacuum. The results according to this procedure indicate that no isomerization or racemization has occurred.

The procedure of converting the enantiomeric carbinols to the chlorides or bromides using thionyl chloride or bromide has the advantage that the enantiomeric R- or S-halides do not need to be distilled for producing the magnesium-organic compound (IV) (FIG. 2), and the later step of carbonation for producing the S- or R-enantiomeric 2-propionic acids (FIGS. 2, 4).

For example, by use of the optically active (+)-1-bromo-1-methyl-2,2-diphenylcyclopropane, an optically active Grignard reagent (H. M. Walborsky and A. E. Young, *J. Amer. Chem. Soc.*, 83, 2595 (1961)), and an active organolithium compound (H. M. Walborsky and F. J. Impastato, *J. Amer. Chem. Soc.*, 81, 5835 (1959)), have been prepared. Significantly, the organolithium compound can be carbonated with 100% retention of optical activity and configuration.

Normally, the scientific data for formation of Grignard compounds are consistent with the "D-model" especially for primary alkyl halides resulting in part of freely diffusing in solution at all times (Garst et al., *J. Amer. Chem. Soc.*, 1985, 108, 2490), hence racemization and low enantiomeric excess are obtained. However, this conclusion cannot be extrapolated to other substrates.

We have found that the reaction of chiral 2-S-(+)-chloro- or bromo-(4-isobutyl-phenyl)-ethane or the corresponding 2-R-(−) enantiomer (FIG. 1 and FIG. 2) reacts almost quantitatively with magnesium in ethereal or THF-solutions at temperatures between 4°–15° C. by keeping the S- or R-configuration without any significant racemization. The same reactions can be carried out in aprotic solvents also, yielding the same results with respect to chemical yields and optical purity by keeping retention of configuration. For carrying out the chemical synthesis, it is not necessary to isolate the S-(+)- or R(−)- Grignard compounds of the corresponding chiral-2-substituted ethane in order to achieve the chiral-2-aryl-alkanoic acids. The enantiomeric 2-alkyl-alkanoic acids, especially those of the 2-alkyl-propionic acids, are readily obtained by passing carbon dioxide through the solution containing the Grignard compounds. It has been found that the yields of Grignard compounds, and the subsequent treatment with $CO_2$, is almost quantitative, and as a rule the optical purities increase with increasing s-character of the orbital involved, which is further substantiated by forming the corresponding mercuric-II-compounds with high optical purity and retention of configuration (FIG. 2). In the case of the stable mercury-carbon bond, the situation can be explained easily by promoting one of the 6 s-electrons to a vacant 6 p-orbital ($4f^{14}5d^{10}6s^2 \rightarrow 4f^{14}d^{10}6s^16p^1$) yielding two half-filled orbitals which are not equivalent. For energy reasons the bond formed from the 6 p-orbital is more stable than the one formed by the 6 s-orbital above because a larger overlap is possible with the 6 p-orbital. A very stable situation is achieved by the mercury compounds of the corresponding R- or S-enantiomers of the halides (FIG. 2) when in the course of bond formation the 6 s- and the 6 p-orbitals combine to form new orbitals (two-sp-orbitals) which are equivalent.

To obtain good chemical yields by retaining configuration in the case of forming the Grignard compounds (FIG. 2, IV) and subsequently converting the magnesium organic chiral compounds to the corresponding carboxylic acids, it is necessary to have clean and very reactive surfaces of magnesium since the adsorbed radicals on the surface of the magnesium (δ-radicals) are retained at the surfaces largely, and they do not dimerize according to our invention, if $CO_2$ is present on the active external surface also. So no dimerization or dispropartionation does occur in ethereal, THF or aprotic solvents, e.g. hexane, benzene, toluene, since the radical is not produced in solution, however, stabilized at the surface of the magnesium metal.

Another way of metallation by retaining configuration with good chemical yields of the corresponding R- and S-enantiomers and subsequent carbonation yielding high optically pure 2-aryl-propionic acids of R- and S-enantiomers can be achieved by reaction with methyl-lithium or n-butyllithium ($CH_3Li$, R-Li) (FIG. 2), also.

The stereoselective insertion of $CO_2$ is of utmost importance for producing metal organic compounds of high optical purities of the corresponding enantiomer with magnesium and/or methyl lithium as well as for the mercuric compounds $R^1$-$HgX_1$ with X=Br, Cl, $CH_3COO$.

It does not necessarily imply that these stereospecific compounds, although new and not being obtained in this high optical purity at present, have to be isolated and subsequently treated with $CO_2$. The formation of the metal-organic compounds according to FIGS. 1 and 2 can be coupled to the treatment with $CO_2$ in one stage, so it is not necessary to isolate the metalorganic compounds.

Another way of using optically high pure enantiomers, R or S, from 1-aryl-haloethane, (FIGS. 3 and 5), being produced easily according to this invention, of 2-aryl-alkanoic acids, especially 2-aryl-propionic acids, is the direct conversion of the 1-aryl-halides with sodium tetracarbonyl-ferrate(-II) ($Na_2Fe(CO)_4$) in the presence of triphenylphosphine ($Ph_3P$) and subsequent oxidation with iodine—$H_2O$ to the corresponding acid, or in the presence of a secondary amine to yield the optically pure amide (FIG. 5). The reagent $Na_2Fe(CO)_4$ can be prepared by treatment of $Fe(CO)_5$ with sodium amalgam (NaHg) in THF.

Figure 6:
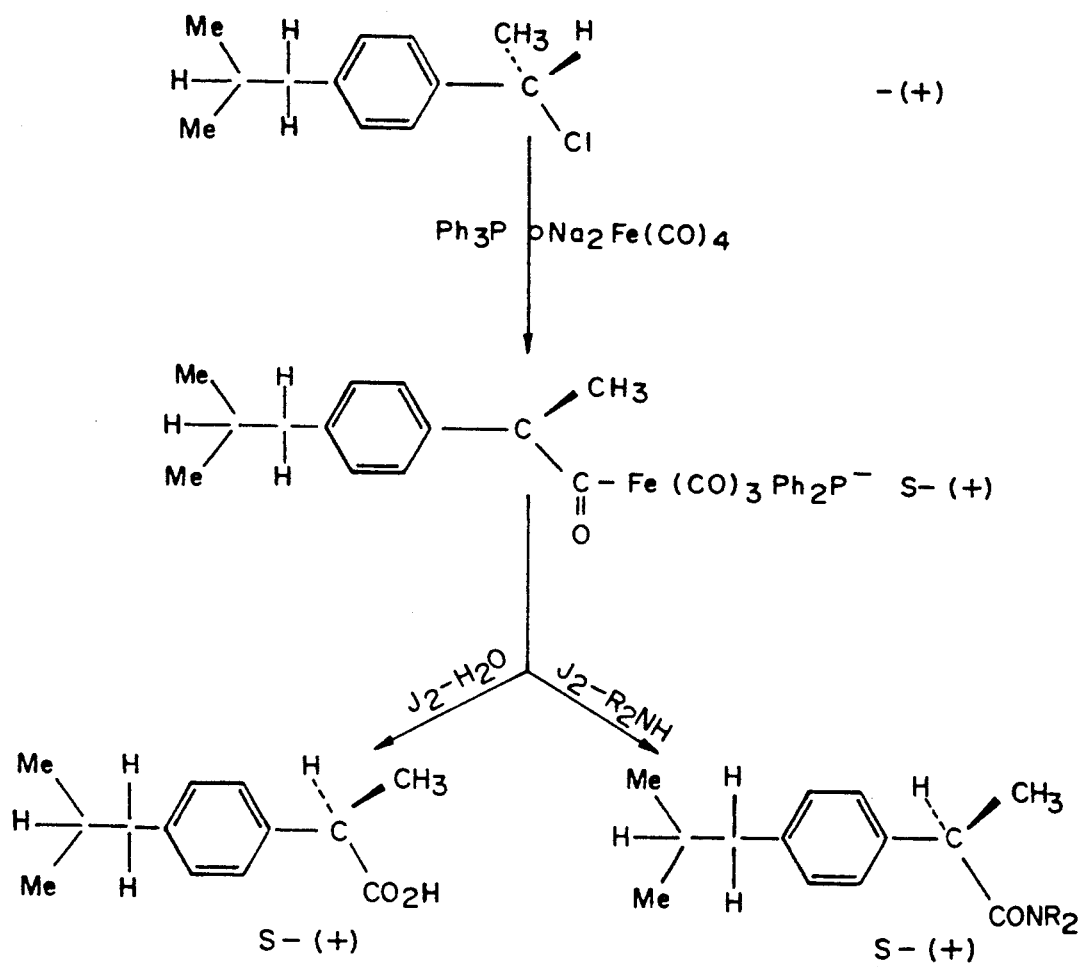

Another method for the conversion of the enantiomeric pure 1-aryl-haloethane (FIG. 2) to the acid derivatives makes use of $Na_2Fe(CO)_4$ also. However, in the presence of CO (FIG. 6), and treatment of the intermediate (IV) with oxygen or sodium hypochlorite and subsequent hydrolysis produces the corresponding enantiomeric acid with high optical purity and chemical yields of 75–80% (see FIG. 6).

Figure 7:
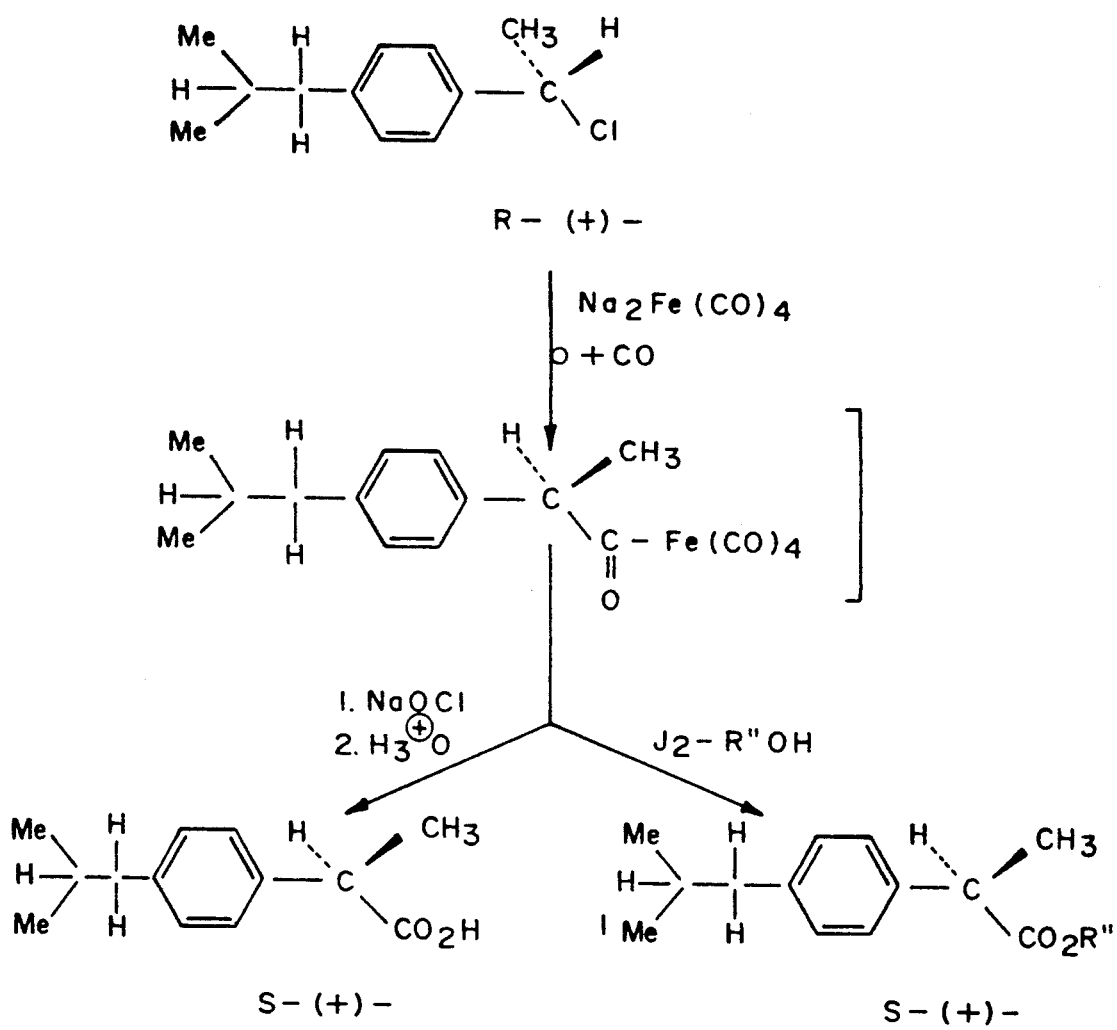

The application of the complex between sodiumtetracyano-ferrate (II) and phosphine (Ph₃P) or carbon monoxide, respectively, is useful especially in the synthesis of 2-alkyl-alkanoic acids, because of its high nucleophilicity and the ease of the integrating inversion reaction of this system. So the halides obtained according to this invention, and the tosylates react with $Na_2Fe(CO)_4$ with typical $S_N$-2 kinetics, stereochemistry (inversion) in order to produce coordinated saturated anionic $d^8$ alkyl iron (0) complexes. According to FIGS. 6 and 7, this procedure provides routes from alkyl and acid halides to alkanes, aldehydes, ketones and stereospecific carboxylic acids, including their derivatives.

A similar method makes use of the conversion of the halides (FIG. 2, IV) to the esters by treatment of the enantiomeric halide (R or S) with nickel carbonyl (Ni(-CO)₄) in the presence of an alcohol, preferably 1-butanol, and its conjugate base, according to the reaction:

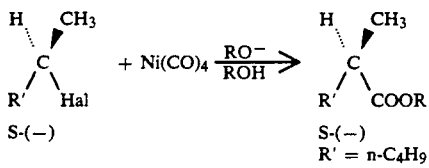

$$R' = n\text{-}C_4H_9$$

The best chemical yields are obtained for Hal=Br, whereas Hal=Cl and I give lower yields (~65%). However, all halides result in high optical purities (>95%).

Figure 8:
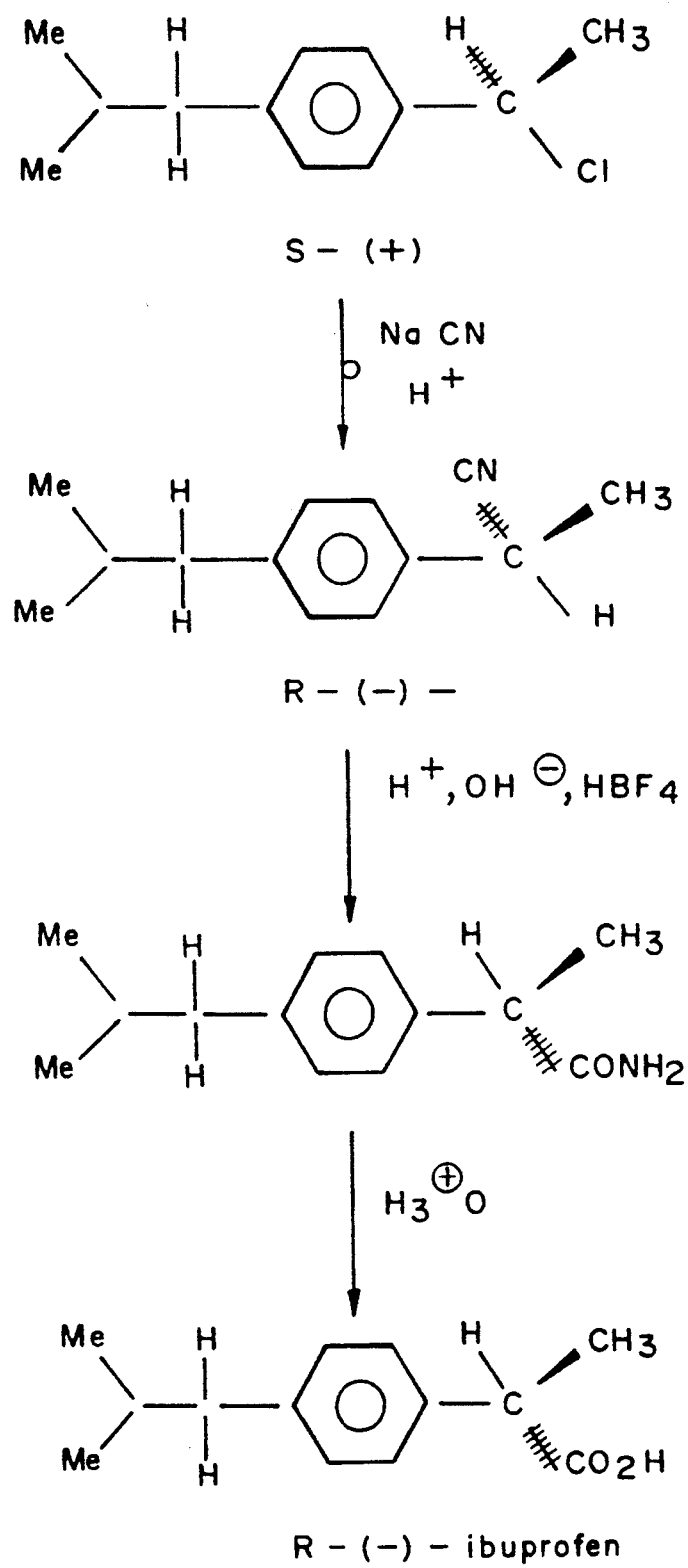
Figure 9:
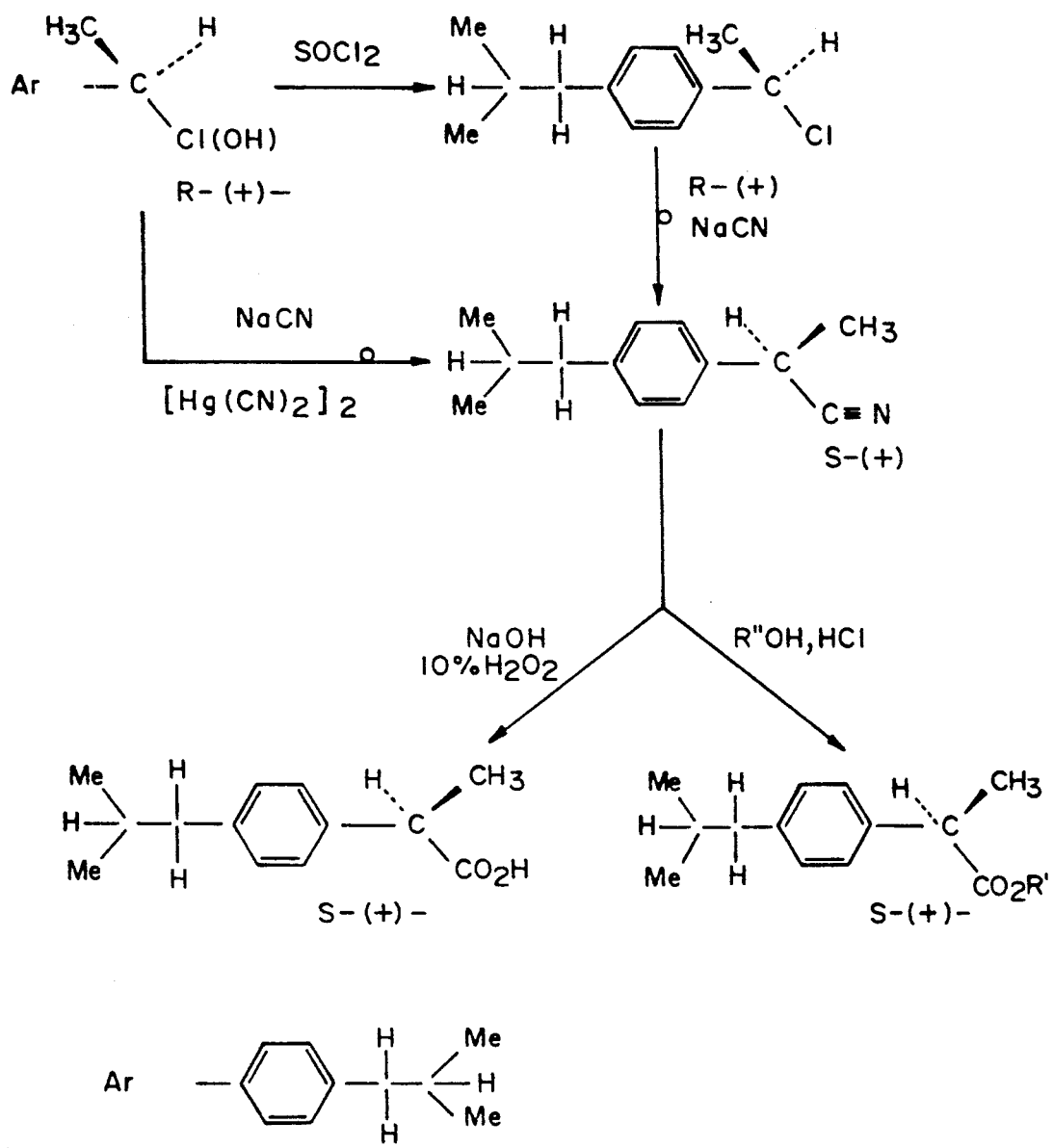

Once having established a stereoselective method of reducing the ketone to the corresponding enantiomeric alcohol with high optical purity (>97%) and very high chemical yields (>90%), it is possible to produce either directly from the R-alcohol the S-carboxylic acids or via the R-form of the halide (FIGS. 2, 8 and 9) the corresponding nitrile in the presence of NaCN and DMSO at 40°–50° C.

Subsequently the enantiomeric S-nitriles can be hydrolyzed to give either amides or the corresponding acids. When the S-acid is desired, the reagent of choice is aqueous NaOH containing about 6–8% $H_2O_2$, though acid-catalyzed hydrolysis can also be carried out successfully. The chemical yields can be improved by using a strong polar aprotic complexing solvent such as HMPT for the synthesis of 2-aryl- propionic acids, or by complexing the cyanide ion as a quaternary ammonium salt. This process has the advantage that the condensation can easily be monitored in a continuous process e.g. as $Et_4{}^+CN^-$, or $C_6H_5.CH_2(Me)_3N^+CN$, applying phase transfer catalysis, or by using crystals such as dicyclohexano-18-crown-6.

The production of the S-enantiomeric nitriles by $Et_4N^+CN$ or Na(K)CN can be performed according to known methods as described by, e.g. J. M. Teulon et al., J. Med. Chem. 21 (9) 901, (1978), N. Tokutake, Chem. Abstracts 88, 50512f; S. Kothicki et al., Chem. Abstracts 90, 1036526; H. Kobler et al., Liebig's Ann. Chem. 1946, (1978); T. Amano et al., Chem. Abstracts, 13, 2611 p; Nissan Chemical Industries, Ltd, Chem. Abstracts, 101 90603e, (1984), Nissan Chemical Industries, Ltd., Chem. Abstracts, 101, 6855 h; J. A. Foulkes and J. Hutton, Synth. Commun. 9 (7), 625 (1979). However, these procedures mentioned lead to racemates, only.

Usually, the 2-aryl-alkanoic acids especially those of the 2-aryl-propionic acids, are scarcely soluble in water; therefore at the end of the reactions the optically active 2-aryl-propionic acids can easily be isolated by filtration, etc. However, avoiding filtration, crystallizations from organic solvents etc., a suitable method for further purification is distillation at high vacuum (~0.06 mm Hg) due to the low melting and boiling points of the corresponding enantiomers of the 2-aryl-propionic acids. Furthermore, a pharmaceutical product as pure as required by U.S. Pharmacopeia is obtained by acid-base treatment of the product isolated by filtration, precipitation or distillation in high vacuum.

The main advantages of the present stereospecific synthesis of 2-aryl-propionic acids from an industrial point of view are as follows:

i) the process is enantio-selective and provides 2-aryl-propionic acids in high chemical yields and with an enantiomeric ratio higher than the epimeric ratio of known synthetic methods;

ii) the reaction solvents are of economically low cost and have safety advantages;

iii) the chiral complexes can be re-used and act at high enantiomeric excess for either enantiomers, R- or S-; so reducing the costs for new chiral complexes;

iv) no further complexes are needed, since the reactions do occur either by retaining configuration, or in case of the production of the optically active nitriles are formed in high chemical yields and high optical purity with no racemization;

v) the auxiliary substances are economical and of low cost;

vi) the different chemical steps can be performed or reduced to two reactors, since the intermediates do not need to be isolated;

vii) the optically active 2-aryl-propionic acids (S or R) can be separated from the reaction mixture by simple filtration, precipitation or distillation in high vacuum;

viii) no high energy costs for carrying out the synthesis on a industrial scale are involved.

A suitable compound formed by the 2-aryl-propionic acid preferably in the S-form for pharmaceutical use is the complex between 1-amino-1-deoxy-D-glucitol (D-glucamine) and the S-(+) 2-aryl-propionic acids. These compounds have the advantages of being water-soluble, they are more lipophilic when used as or in transdermal delivery systems and do reveal antimicrobial activities in vivo and in vitro due to their surface activity and form mixed micelles with phospholipids.

Figure 10:
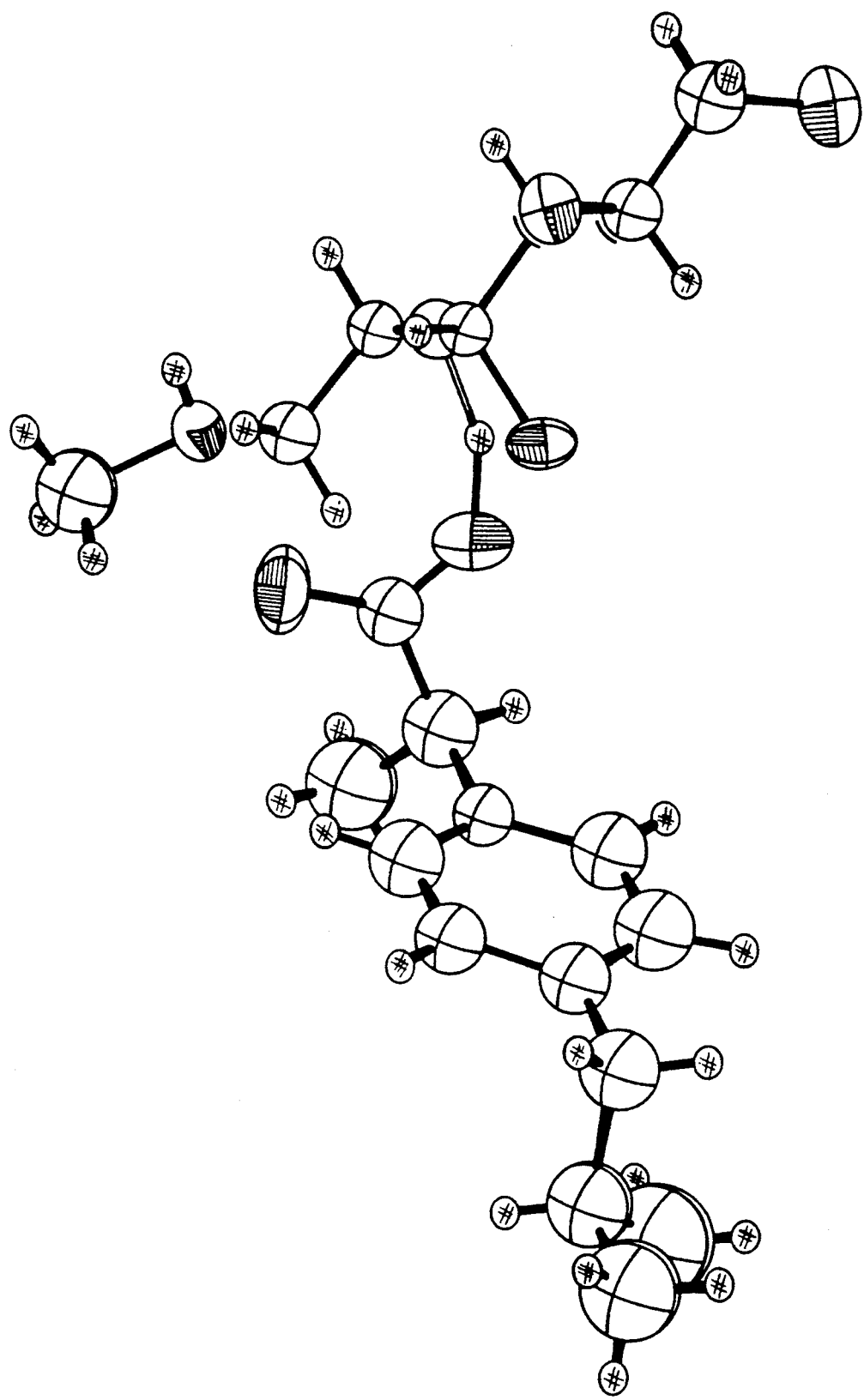

It has been found, for example, that 1-amino-1-deoxy-D-glucitol forms, e.g. with R-(−)-ibuprofen a 1:1 complex that is hydrogen bonded (FIG. 10). The crystal has cell dimensions of a=8.275 Å, b=40.872 Å, and c=6.420 Å, with four molecules in the unit cell, having the space group P $2_12_12_2$ (#19). The complex structure of the 1:1-complex reveals a strong bond between the hydrogen of the carboxo group of the S-ibuprofen and the O₃-oxygen of the 1-amino-1-deoxy-D-glucitol with no involvement of the hydrogen of the 1-amino- group (FIG. 10), similar to the S-(+)- ibuprofen-D-glucamine complex.

Figure 11:
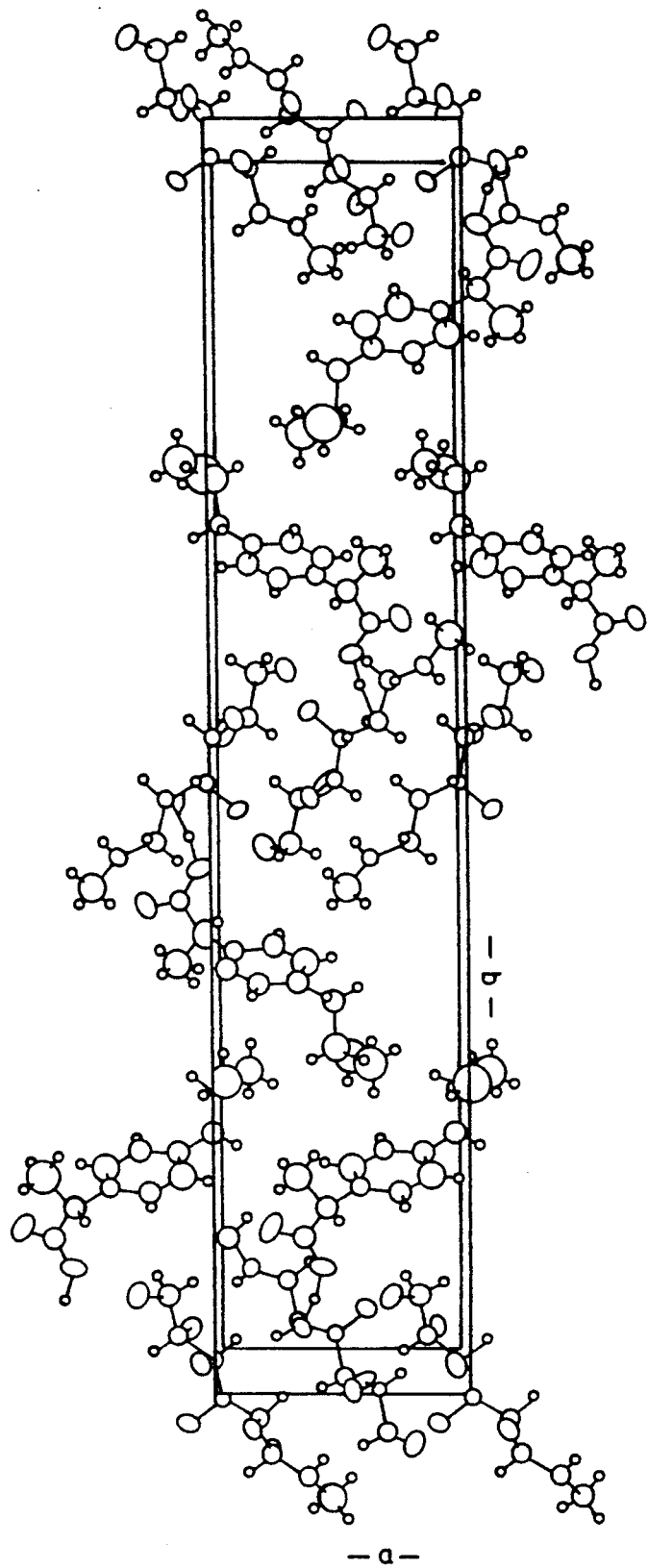

The (R, S)-ibuprofen forms a 1:1-complex also, showing both enantiomeric (S)-(+)ibuprofen-D-glucamine structure as well as the corresponding R-(−)-ibuprofen-D-glucamine structure (FIG. 11).

Figure 12:
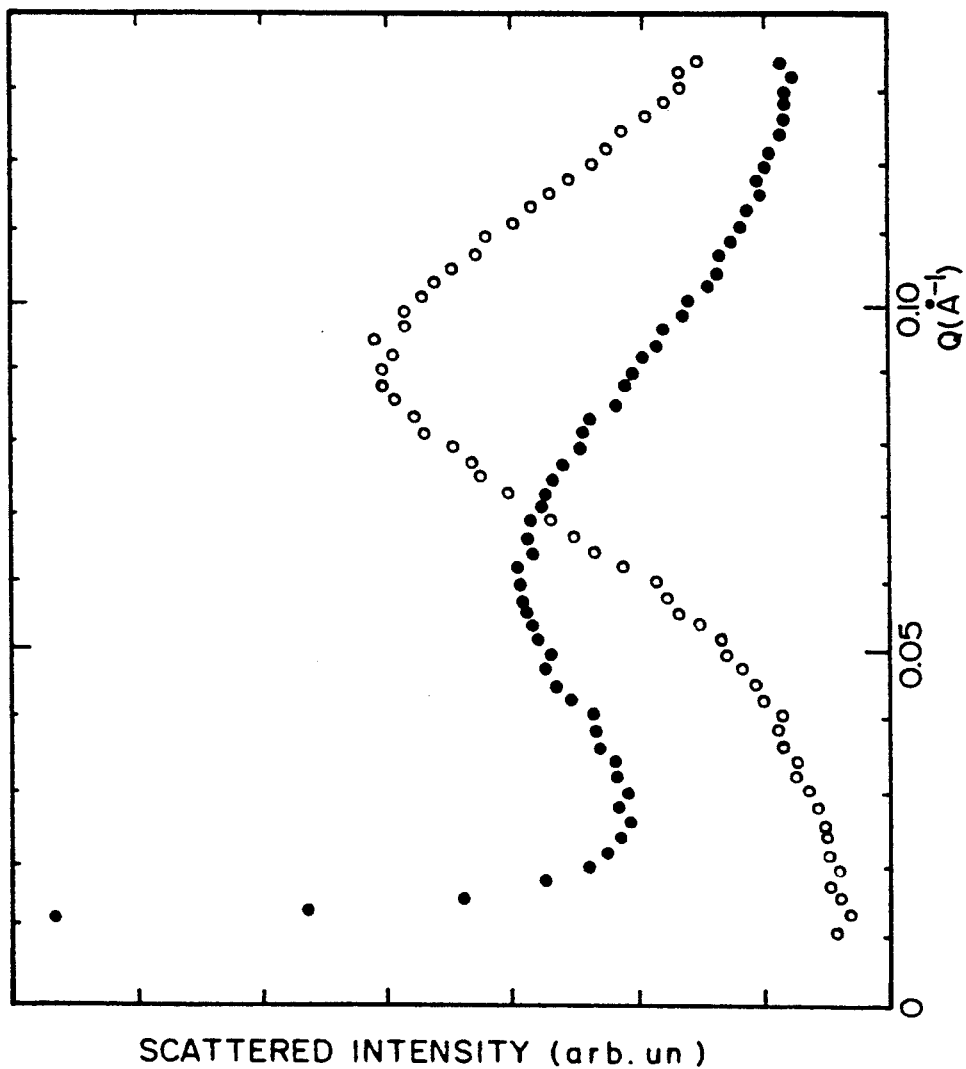
Figure 13:
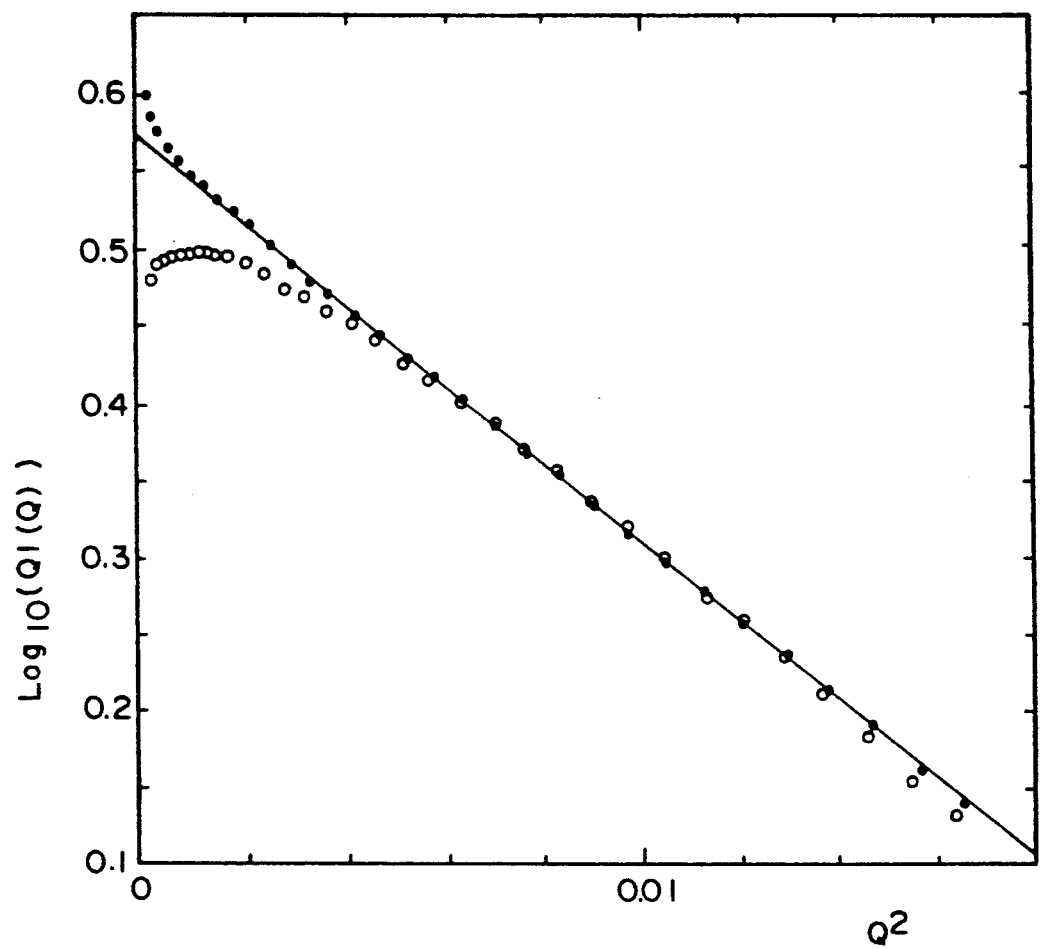

Having established the stoichiometric complexes between S-(+)-ibuprofen and D-glucamine or D-ribamine, it is possible to prepare a pharmaceutical formulation on the same chemical basis, e.g., interaction between the carboxylic acids and the hydroxyl of the D-glucamine, in a melt. The resin of such melt is, e.g., polyoxyethylene glycolates, polyoxyethylene units in general having an average molecular weight of 400 to 6000, at most. Polyoxypropylene oxides are very useful, also, since they are able to provide acceptors for hydrogens delivered from the carboxylic acids due to deprotonation, forming very stable hydrogen bonding between the 2-aryl-alkanoic acids and this matrix. There are several advantages of such a pharmaceutical formulation over microcrystals of the pure drug, e.g., S-(+)-ibuprofen, dissolution properties, filling in hard capsules due to easy handling, and importantly the S-(+)-ibuprofen, naproxen and other 2-aryl-propionic acids of the enantiomeric pure state do behave physically the same in the melt as well as in aqueous solutions yielding a semidilute molecular solution of, e.g., S-(+)-ibuprofen within the melt. This unexpected behavior in the melt as well as in aqueous solution which is provided by scattering experiments and will be described in conjunction with an example, provides stability of S-(+)-ibuprofen and retention of chiral configuration without any racemization which occurs, e.g., on putting pressure on R-(−)-ibuprofen tablets, or microcrystals due to changing of the molal volume of the R-enantiomeric form. This can happen to S-(+)-ibuprofen microcrystals upon pressure also, so it is desirable to have a solid pharmaceutical formulation which inter alia avoids these disadvantages. Furthermore, the resin built up of polyoxyethylenoxide units having a chain length corresponding to molecular weights between 400-6000 normally have melting points of about 50°-55° C., can dissolve completely S-(+)-ibuprofen as a molecular solution in the melt. The drug behaves in this melt as a molecular solution of a solute (drug, e.g. S-(+)-ibuprofen, S-(+)naproxen) in a solvent (polyoxyethylenoxide) according to the laws of solution chemistry in a physical sense. This implies that there is no segregation of S-(+)-ibuprofen from this melt, unless the solid solution is oversaturated by the drug. These isotropic solutions of S-(+)-ibuprofen in polyoxyethylenoxide (solvent) in the melt as well as diluted in the aqueous media can be followed by small-angle X-ray and neutron scattering, and can be compared to the solid state of the melt also (FIGS. 12 and 13).

Especially, chiral compounds applied as medicinal drugs in certain pharmaceutical formulations can cause difficulties, e.g. racemization, changing in a different polymorphic physical form, deterioration of the enantiomeric, active drug, as well as undesired side effects with regard to in vivo and in vitro dissolution. In order to improve stability, retention of configuration upon pharmaceutical formulation with respect of pure enantiomeric 2-aryl-alkanoic acids, e.g. S-(+)-ibuprofen, S-(+) naproxen, including suitable dissolution rates in vitro and in vivo, it has been discovered that these achievements can be accomplished by dissolving enantiomeric pure 2-aryl-propionic acids in a melt, consisting of polyoxyethylene glycol, poloxyethylenoxide or mixtures of these having weight average molecular weights between 300 to 6000. In addition, these resins are mostly water soluble when coming into contact with watery solutions e.g. emulsions, suspensions including microemulsions and in matrixes with oil in combination with wax or paste which are normally used for fillings in soft gelatin capsules. These, and other non-aqueous solutions, emulsions, etc. of pharmaceutical interest are described by Schick et al., "Emulsions and Emulsions Technology," Vol. 6, *Surfactant Science Series*, II, Chapter 13, "Cosmetic Emulsions," 1974, 729-730, ed. J. Tissaut—Marcel Dekker Inc., N.Y., U.S., M. J. Schick in "Nonionic Surfactants," *Physical Chemistry*, 1988, Marcel Dekker, Inc. N.Y., and Basel. The EP-No.: 83109839.4 "Anhydrous Emulsion and the Size Thereof" teaches the preparation of a pharmaceutical preparation which melts at 37° C., however, on the physical chemical basis of a emulsion. However, they do have the disadvantage of leaking when filling hard gelatin capsules due to thixotropic processes.

This newly described process for a melt in a suitable matrix containing certain amounts of enantiomeric 2-aryl-alkanoic acids or 2-aryl-propionic acid has the advantages of being i) a real solution in the physical sense; ii) a very reliable dosage form of high homogeneity as one finds in real physical solutions; iii) easy to handle technically when using hard gelatin capsules; iv) resistant to demixing - phenomena on a molecular basis; v) capable of yielding favorite in vitro and in vivo dissolution and vi) capable of rapid resorption of the drug.

The surface activity of the enantiomeric 2-aryl-propionic acids are bound only to the S-form. This particular activity can be enhanced by complexation with D-glucamine as stated above or with D-ribamine, as well as by cationic detergents, especially by n-hexadecyl-pyridinium or benzethonium cations through binding at the carboxo-groups of the S-2-aryl-propionic acids. The enhancement of the surface activity and therefore the antimicrobial activity is related to the hydrophobic chain of the hexadecylpyridinium or benzethonium residues due to their low critical micelle concentrations (CMC) of approximately $1.5 \times 10^{-5}$ Mol/1 when complexed with, e.g. S-(+)-ibuprofen. An advantage of this pharmaceutical formulation is a dosage reduction due to faster penetration of the S-(+)-ibuprofen through membranes, skin and reaching the target cells faster due to micellisation and targeting of the S-(+)-ibuprofen. Therefore, from a medicinal point of view the use of the complexes between 2-(S)-aryl-propionic acids or alkanoic acids with cationic detergents, D-glucamine or D-ribamine reduces the dosage of the non sterodial substances brought about by the vehicle function of the cationic surfactants or D-sugar-alcohols, superior than using simply alkali or earth alkali metals as well as (S, R)-lysin salts of 2-aryl-alkanoic acids.

Figure 14:
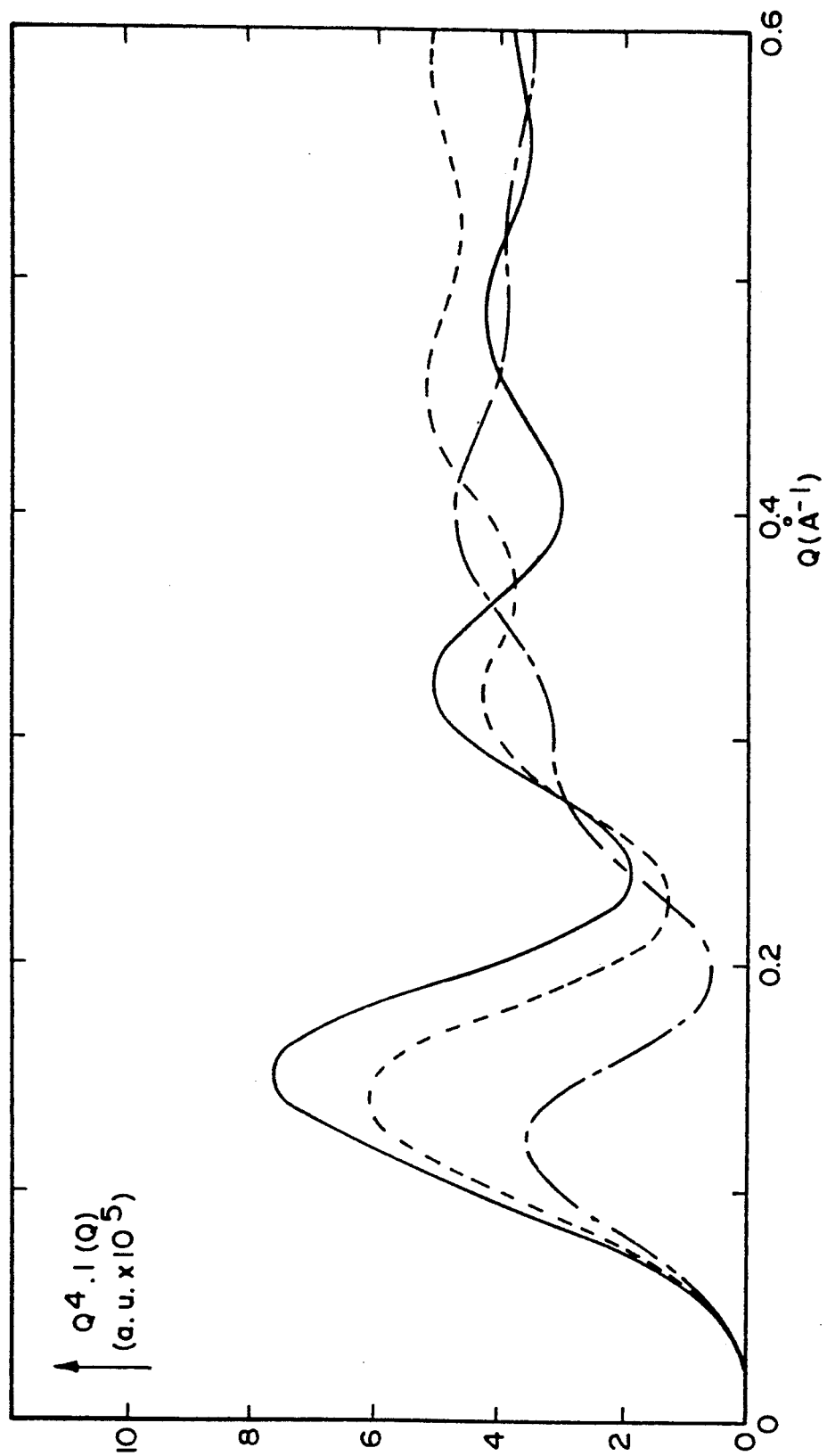
Figure 15:
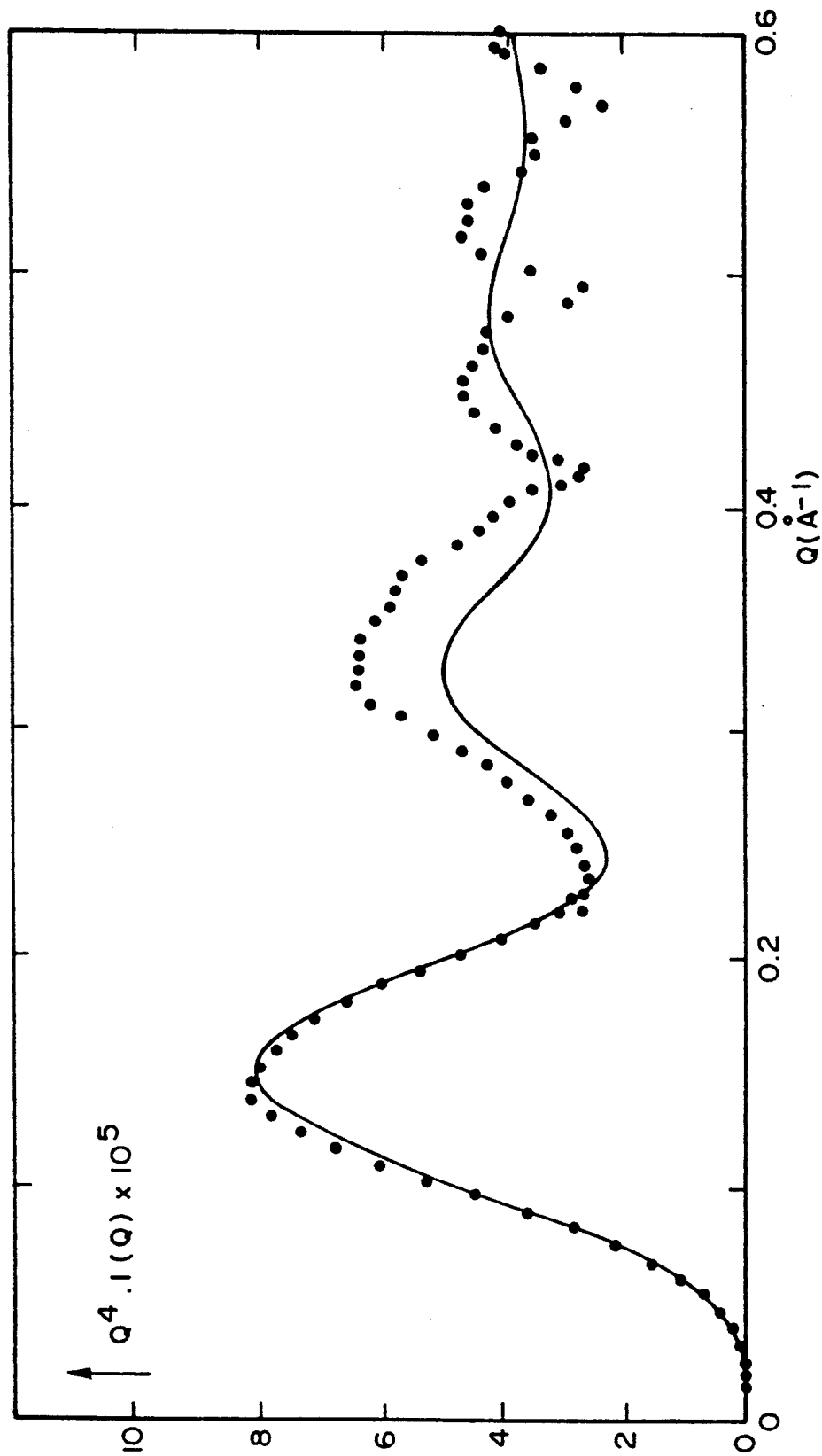

X-ray diffraction patterns as well as small-angle X-ray scattering profiles (FIGS. 11, 12) reveal unstructured behavior in a sense of diffuse scattering. Therefore, it is possible to treat the scattering data at high and low scattering angles in a thermodynamic way in addition to the overall electron distribution of the polyoxyetheylene chain (matrix) and solubilized drug, e.g. S-(+)- or R-(−)ibuprofen. It has been discovered that the scattering curves of the melt (ligand) containing the matrix and the drug (S-(+)-ibuprofen) dissolved in the melt, have the same scattering profile when the solid melt is dissolved in aqueous media. Importantly, it has been discovered that a certain degree of clustering of S-(+)-ibuprofen or S-(+)-naproxen molecules has taken place in the liquid melt as well as in the solid melt, partly along the hydrophilic linear macromolecules such as PEG 1500 or polyethyleneoxides. It has been found that in the liquid melt the weight-average molecular weight, MW$_{app}$ is of the order 25,000+/−5,000, similar for the solid melt and the one in aqueous solution in the presence of S-(+)-ibuprofen. The weight-average radius of gyration, Rg, is determined to be of the order Rg=45.0=/−5.0 Å, equivalent of a zig-zac or meander conformation of the linear linked —CH$_2$ or —OCH$_2$-units. Upon addition of S-(+)-ibuprofen or another enantiomeric 2-aryl-alkanoic acid MW$_{app}$ is a function of the concentration of the enantiomeric drug which can be described through changes of the second virial coefficient and the isothermal compressibility coefficient of a one-component solution. The decrease on the value of the second virial coefficient observed for S-(+) or R-(−) ibuprofen is related to an increase of the included volume of the enantiomeric form within the melt. The molecular explanation for this unexpected solution behavior in the melt (solid, liquid) and in aqueous solution is the binding of exposed hydrophobic regions of enantiomeric 2-aryl-propionic acids, e.g. isobutylbenzene or naphthylgroups, to CH$_2$-groups. The free energy$\Delta$G of this particular binding of the enantiomeric drugs of the 2-aryl-propionic acids is of the order of 0.5–0.7 k$_B$.T per PEG molecule, for S-(+)-ibuprofen a value of 0.56 k$_B$.T/PEG or 0.50 k$_B$.T polyoxyethylene unit has been determined. Similar values, although different as found for the S-enantiomers, were discovered for R-(−)-ibuprofen of 0.45–0.51 k$_B$.T per PEG molecule or 0.46 k$_B$.T per —CH$_2$O-unit. The racemate has a $\Delta$G-value of 2.5 k$_B$.T/PEG, very different from the pure enantiomers. A very likely geometric description of this melt as well as where dissolved in aqueous solution is that of a necklace chain. The random coils of the PEO- or PEG-units are wrapped around the hydrophobic cores of the S-(+)-ibuprofen or naproxen molecules whereas the hydrophilic carboxylic acid is located close to oxyethylene (—CH$_2$-O)-units or (CH$_2$)O-units of the PEG. The protons of the 2-aryl-propionic acids stereoisomers are switching between the ethereal or hydroxo-groups of the PEO and PEG molecules, respectively, and the carboxo groups, as can be shown by FT-IR-investigations also. This situation is also met when going into aqueous solutions, supported by the interaction of water molecules with the PEO and PEG residues, protecting the 2-aryl-propionic acid steroisomers against pH, undesired protonation, racemization at alkaline pH, and keeping retention of configuration. The scattering curves (FIGS. 12 and 13) of the solid melts, e.g. PEG or PEO with the solubilized S-(+)-ibuprofen do not show any interparticle interference effects, even when performing the experiments in aqueous solutions. It has been discovered that these particular melts, containing S-(+)-ibuprofen do not show any demixing phenomena when liquid, with increasing temperature as does PEG and PEO in aqueous solution. Interestingly, this is also found in aqueous solutions also, when the melts (solid) go into solution between 37°–40° C.; normally mixtures of this kind do separate with increasing temperature (phase-separation), depending on the components of the mixture when reaching the phase-separation temperature. This is not the case as observed in this invention, since the repulsive forces due to the addition of the enantiomeric 2-aryl-propionic acids are being reduced in the melts as well as in aqueous solutions. This is also manifested through the recording of the scattering curves at high scattering vectors of the melts (FIGS. 14, 15).

The following examples are given further for purely illustrative purposes of this invention without in any way limiting the same.

All synthetic procedures for obtaining the enantiomeric 2-carbinols have to be carried out in the absence of moisture, preferably under nitrogen atmosphere.

The (+)-(2S,3R)-4-dimethylamino-3-methyl 1,2-diphenyl-2-butanol (R*OH) should have an $[\alpha]_D^{27}$ +8.00° (c 9.52, EtOH), mp 56° C., and stored in an desiccator over P$_4$O$_{10}$ in the presence of N$_2$. This alcohol can be recovered from the hydrochloride and can be repeatedly reused. The solvents, ether (Et$_2$O), THF, 1,2-dimethoxy-ethane and benzene are distilled over LiAlH$_4$ and should be stored over molecular sieves. The stock solutions of LiAlH$_4$ should be stored under N$_2$, and passed through a glass filter (1G2) under N$_2$ before use.

EXAMPLE 1

Preparation Of R-(+)-2-(4-Isobutyl-Phenyl-)Hydroxyethane 10 g of R*OH are dissolved in 10 ml Et$_2$O at 0° C., and 10 ml of a 1M solution of LiAlH$_4$ are added to the ethereal solution of R*OH at 0° C., under continuous stirring; a white pasty precipitate develops at 0° C. It is important that this precipitate be well stirred, so a white, homogeneous suspension can develop. After forming the R*OH.LiAlH$_4$ complex which should be completed within 5 minutes at 0° C., 10 g (5 mmol) of 1-(4-[2-methylpropyl]-phenyl) ethanone dissolved in 10 ml ether 0° C. are added dropwise to the suspension under continuous mixing by keeping the temperature between 0° C. to 5° C. constant for one hour. The suspension gives a clear colorless solution after adding the ketone which is left for completing the reaction for 12 hours under continuous mixing between 0°–5° C. This mixture is hydrolyzed with 0.5 ml of water, and diluted with hydrochloric acid which is added in order to dissolve the R*OH for later reuse. Mixing is continued for two hours at 20° C., until a transparent solution is achieved again.

The clear solution is extracted with Et$_2$O, leaving R*OH.HCl in the aqueous phase, and the R-(+)-2-(4-isobutyl)hydroxyethane in the organic phase. The ethereal extracts are combined, concentrated and distilled in high vacuum (0.1 mm Hg; b.p. 80° C.) which gives a clear, colorless fairly viscous liquid (1.15 g, 94% yield), containing no unreduced ketone as measured by HPLC-techniques and confirmed by the absence of the carbonyl infrared stretching frequency. The optical purity is determined by conversion to the MTPA derivative and by measuring the NMR-spectrum gives a value of 98% e.e.

Neutralization of the acid extract yields recovered chiral R*OH with $[\alpha]_D^{20}$+8.21° (C 11.0, EtOH).

It is observed that addition of molecular sieves, e.g. as zeolites, increases the kinetics of formation of the enantiomeric R (+)-carbinol at 0° C., from the reduction of the 1-(4-[2-methylpropyl]phenyl) ethanone. 5 g of R*OH are dissolved in 5 ml Et$_2$O, or THF, benzene, 1,2-dimethoxy ethane, toluene, in the presence of 0.2 g commercially active 4A molecular sieves, and heavily stirred under a stream of N$_2$. To this mixture a solution of 5 ml of a 1M solution of LiAlH$_4$ is added at 0° C., under continuous mixing. The reaction time for converting the unsymmetrical ketone to the corresponding enantiomeric R-carbinol can be reduced to two hours or less. For technical reasons the molecular sieves can be centrifuged and reused as well as R*OH as described above.

In another procedure the ketone is added immediately after forming the reagent, R*OH.LiAlH₄, in the presence of the molecular sieves, which has the advantage that no unreduced ketone is present in the R-carbinol produced. This is especially important to achieve almost quantitative chemical yields of unsubstituted R-1-naphthylhydroxyethane, or R-1-[2-fluoro-4-diphenyl]-hydroxyethane, R-1-[4-chloro-2-phenyl]-hydroxyethane, R-1-[6-hydroxy-2-naphtyl]-1-hydroxyethane and R-1-[6-methoxy-2-naphthyl]hydroxyethane.

EXAMPLE 2

Preparation Of S-1-(4-Isobutylphenyl)-Hydroxyethane 10 g of R*OH (35 mmol) are dissolved in 20 ml Et₂O, and 15.6 mmol of LiAlH₄, dissolved in 30 ml of Et₂o are added and stirred at 20° C. in the presence of 0.2 g molecular sieves. The suspension is refluxed for 10 minutes under continuous stirring in the presence of the molecular sieves. The solution which should have clear supernatant in the presence of the molecular sieves is stored at 20° C. for 20-24 hours in case of no rapid mixing; however, upon rapid mixing at 20° C. the formation of the chiral complex in the presence of molecular sieves is complete after two hours. The reduction is carried out as described above by adding dropwise 10 mmol (2.0 g) of 1-[4-(2-methylpropyl)]phenyl-ethanone and leaving the solution to react for 8 hours. The reaction time with respect to reduction to the corresponding S-(−)carbinol can be decreased by rapid mixing in the presence of the molecular sieves without raising the temperature above 20° C. The processing of the S-(−)carbinol is the same as described above.

The optical purity is determined to be 97% as determined by NMR methods and the chemical yield of pure product is almost 95%.

The reduction of the ketone can be performed in aprotic solvents, also, e.g. benzene, toluene or hexane. In order to have good chemical yields of enantiomeric carbinols it is necessary to perform these reactions under vigorous stirring in the presence of molecular sieves and glass beads. The reaction times, modes of addition of the unsymmetrical ketones, ratio of R*OH to LiAlH₄ and temperature conditions are the same as described above.

The reduction described above can be carried out in well stirred, continuous tank reactors because it is particularly suitable for liquid phase reactions in large scale industrial productions. It gives a consistent product quality (optical purity) ease of automatic control and low man power requirements. Since in a stirred tank reactor the reactants, e.g. R*OH.LiAlH₄ and the ketone, are diluted immediately on entering the tank which favors the desired reaction (constant ratio of LiAlH₄ R*OH) and supresses the formation of by-products, volume and temperature of the tank are readily controlled, so hot spots are less likely to occur, especially in the presence of molecular sieves when the continuous stirring is well adjusted.

The chemical yields are of the order of 85-98% in the absence of moisture and high vacuum distillation of the enantiomeric carbinols.

EXAMPLE 3

Reduction Of The Ketone With (−) 2,2-Dihydroxy-1,1-Binaphthyl To S-(−)-1-(4-Isobutylphenyl)-Hydroxyethane To a 1.5M THF solution or LiAlH₄ (8.0 mmol) under nitrogen atmosphere in the presence of molecular sieves (0.2 g 4A zeolites) ethanol in THF (2M, 8.50 mmol) are added at 0° C. This solution is continuously stirred when S-(−)-2,2'-dihydroxy-1,1-binaphthyl reagent (8.5 mmol) THF (0.64 mmol) is added at 0° C. After addition of the S(−)-2,2'-dihydroxy-1,1-binaphthyl reagent at 0° C., the solution is stirred continuously for one hour at 20° C. without having developed a white precipitate as observed normally. The chiral reagent formed is cooled down to −20° C., and 2.50 mmol of 1-[4-(2-methylpropyl)] phenyl-ethanone, dissolved in THF (1M solution) is added under continuous mixing and kept for 8 hours at −20° C. under continuous stirring. The reaction is stopped by adding 1.0N HCl at −20° C., the chiral reagent recovered, and the work-up with ether followed by distillation afforded optically pure S-(−)-1-(4-isobutylphenyl)-hydroxyethane, 310 mg, 81%, in an optical yield of almost 95% in enantiomeric excess and configuration. The chiral reagent can be be reused after recrystallization from benzene without any noticeable racemization.

EXAMPLE 4

Preparation Of S-(+)-2-[4-Isobutylphenyl] Propionic Acid 10 g of S-(−)-1-[4-isobutylphenyl]-hydroxyethane (56 mmol) are dissolved in 20 ml 1.4 dioxane at 20° C. in the presence of molecular sieves 4A under stirring. 5.0 ml SOCl₂ (=60 mmol), dissolved in 5 ml 1.4-dioxane, is added dropwise under continuous stirring over a period of 10 minutes by keeping the temperature at 20° C. After one hour the reaction is complete and the thionylchloride is recovered through evaporation by bubbling N₂ through the solution. The S-(−)-1-[4-isobutylphenyl]-chloroethane does not need to be separated since the solution is used immediately for metallation with Mg or Hg (OOC CH₃)₂. To this solution containing 11 g of S-(−)-1-(−)-[4-isobutylphenyl]-chloroethane 1.40 g Mg (0.055M) in the presence of iodine is added at 0° C., and after a period of 10-30 minutes a vigorous reaction starts, so sometimes cooling may be necessary in order to avoid Wurtz synthesis and biradical production. The solution turns from light yellow to light brown at the end of the reaction when carbon dioxide is passed through the reaction at 0°-5° C., under continuous mixing. The Grignard compound which is derived from S-(+)-1-[4-isobutylphenyl]chloroethane (or bromoethane when SOBr₂ is used) is diluted by Et₂O or THF (or benzene, toluene) when passing dry CO₂ through the solution under continuous stirring which is essential for obtaining high chemical yield of optically pure S-(+) ibuprofen. The continuous addition CO₂ to the S-Grignard compound and the production of the S-carboxylic acid makes it necessary to add dry 1,4 dioxane continuously as the S-carboxylic acid develops and saturates the solvent. After 20 minutes the reaction is complete, is separated from solid residues and is transferred to high vacuum distillation. The solution is concentrated and distilled at 2 mmHg (0.06-2 mm Hg) at 120°-98° C., to give 9.30 g (80%) of S-(+) ibuprofen: NMR (CDCl₃) S 0.91 (d,J=7H, 6H), 1.50 (d,J=8 Hz, 3H), 1.84 (nonet,1H),2.96 (brd, 27H7,2H),3.72(g, 1H),7.01–7.32 (AA'BB',4H), 9.78 (br. sl H). $[\alpha]_D^{25} + 58°$ (95%, EtOH).

EXAMPLE 5

Preparation Of R-(−)-2-[Isobutylphenyl]-Propionic Acid

The same procedure can be performed as outlined in Example 3. However, the R-(+)-1-[4-isobutylphenyl]-chloroethane can be easily produced from S-(−)-1-[4-isobutylphenyl]-hydroxyethane by reacting SOCl₂ in pyridine in the presence of water. 10 g of S-(−)-1-[4-isobutylphenyl]-hydroxyethane (56 mmol) is dissolved in 15 g pyridine, containing 10% (w/w) water at 20° C. Under continuous mixing 6.7 g SOCl₂ (equivalent to 4.1 ml) is added and refluxed for 20 minutes. After removing the excess of SOCl₂ and pyridine (b.p. 116° C., 760 mmHg) the chloride is distilled at 6 mmHg (bp 98.3° C.) to give 9.59 g of R-(+)-1-[4-isobutylphenyl]chloroethane (86.6%): NMR (C Cl₄) $\delta$0.90 (d,J,7 Hz,6H), 1.84 (d,J7 Hz,3H), 1.86 (nonet, 1H), 2.48 (d,J=7 Hz,2H), 5.15 ( q, 1H),7.10–7.44 (AA'BB'4H). Analysis: calc. for $C_{12}H_{17}jCl$:C 73,26;H,8.7 , Cl, 18.01, found: (73,40% H: 8.79% Cl 18.09% $[\alpha]_D^{25} - 29.5°$ (C 1.9%, (CCl₄);

The corresponding Grignard reagent (0.9M–1.5M) in Et₂O is prepared in approximately 80% yield by adding slowly a solution of the halide in Et₂O to magnesium at 4° C. as described above in Example 3. The procedure for carbonation or mecuration in the presence of Hg(OOCCH₃)₂, [Hg (CN)₂]₂ or HgCl₂ is similarly as described in Example 4. The chemical yield of R-(−) ibuprofen is 78% and the optical purity almost 98%.

EXAMPLE 6

Synthesis Of S-(+) Ibuprofen Via Nitrile And Subsequent Hydrolysis 10 g R-(+)-1-[4-isobutylphenyl)-chloroethane (50.5 mmol) are dissolved in 25 ml EtOH and 15 ml water, and reacted with 2.95 g (60 mmol) sodium cyanide dissolved in 10 ml water under dropwise addition of the cyanide solution under continuous stirring. The mixture is refluxed for one hour and allowed to cool down to 20° C. The precipitated sodium chloride is filtered off and the supernatant, containing water and EtOH are dried and EtOH is distilled from the remaining liquid, which contains the S-(+)-1-[4-isobutyl phenyl]-ethyl cyanide. (Chemical yield 88%). This S-(+) cyanide is dissolved in 15 ml EtOH and 30 ml water, which contains 9 g (0.45 mol) sodium hydroxide and 10% (w/w) H₂O₂ and heated under reflux conditions for one hour. After cooling to room temperature the reaction mixture is diluted with 100 ml water until a clear and transparent solution appears. This solution is cooled down to 0° C. and 100 ml of diluted hydrochloric acid is subsequently added, when S-(+)-ibuprofen precipitates as small crystals. The S-(+)-ibuprofen crystals are collected, washed with dilute hydrochloric acid and dried over Ca Cl₂. The chemical yield is 94% and the melting point was 51°–54° C. $[\alpha]_D^{20} + 60°$ (95% EtOH).

EXAMPLE 7

Synthesis Of S-(+)-Ibuprofen From The R-(+)-1-[4-IsobutylPhenyl]-Chloroethane With Sodium Tetra Carbonyl-Ferrate And Carbon Monoxide 10 ml R-(+)-1-[4-isobutylphenyl]-chloroethane (50.5 mmol) are dissolved in 150 ml of dimethyl formamide (DMF) (0.033M) under rapid mixing and N₂-stream, 10.8 g sodium-tetracarbonyl-ferrate-II which is freshly prepared by treatment of iron-pentacarbonyl Fe(CO)₅ with sodium amalgam and THF at 20° C., are added by continuous mixing. The solution is cooled down to 10° C. and a stream of carbon monoxide is passed through the solution. Normally, the reaction is finished after 1–2 hours, depending on temperature and solvents (THF, DMF,DMSO); however, it can easily be monitored when an excess of carbon monoxide is leaving the solution in the presence of N₂. The oxidative cleavage to the corresponding S-(+)-2-[isobutyl phenyl] propionic acid is achieved by adding an aqueous solution of sodium hypochloride with subsequent addition of 0.1M hydrochloric acid by keeping the reaction temperature at 10° C. Care must be taken to add enough hydrochloric acid since most of the protons are used for precipitation of S-(+)-ibuprofen in aqueous solution for recovery of the free acid.

The corresponding amide from S-(+)-ibuprofen can be prepared by using triphenyl phosphine (Ph₃P) instead of carbon monoxide in the presence of sodium tetracarbonyl ferrate (II)(Na₂ Fe(CO₄)). 10 g of R-(+)-1-[4-isobutyl phenyl]-chlorethane are dispered in 30 ml benzene in the presence of 10.8 g sodium tetracarbonyl ferrate-(II) at 20° C. 13.4 g triphenyl phosphine (0.051 mol) dissolved in dry benzene are added dropwise during a period of time of 20 minutes under N₂ atmosphere. The mixture is refluxed under continuous stirring for three hours, the reaction mixture is left standing for one hour at 20° C. with subsequent quenching of the reaction with methyl-benzylamide. The small crystals of S-(+)-ibuprofen methyl benzylamide are filtered off, recrystallized from THF/DMF, and analyzed by HPLC-methods for optical purity: the HPLC-analysis shows the presence of 98% diastereisomer corresponding to S-2-(4-isobutyl phenyl) propionic acid at retention times of 2.79 minutes and 2% diastereisomer corresponding to R-2-(4-isobutyl phenyl) propionic acid at retention times of 2.38 minutes. The chemical yields for producing the S-2-carboxylic acid from the corresponding R-(+)-1-[4-isobutyl phenyl]-chlorethane are, in the presence of carbon monoxide, almost 95% with an optical purity of 95–98%, and 90% in the presence of triphenyl phosphine, respectively.

EXAMPLE 8

Preparation Of Complexes Between S-(+)-Ibuprofen And 1-Amino-1-Deoxy-D-Glucitol 206.27 (250.0) mg S-(+)-ibuprofen and 236.72 (181.19) mg of 1-amino-1-deoxy-D-glucitol are dissolved in 6 ml of water, subsequently treated at 45° C., and sonified for one hour. The clear solution can be stored and used for medical practice after sterilization. The complex can be crystallized from ethereal or alcoholic solution by adding these solvents at 20° C., under continuous stirring to an aqueous solution of S-(+)-ibuprofen and 1-amino-1-deoxy-D-glucitol (pH 7.5). the microcrystalline precipitate can be collected by filtration with subsequent drying over CaCl₂ under N₂-atmosphere. In addition, if no crystalline precipitate can be certified, the supernatant is discarded and the precipitate is dried over P₂O₅/CaCl₂ in vacuo at 30° C. The melting point of the amorphous complex is 61° C.; of the crystalline specimen is 106.5° C. By applying other precipitating solvents, e.g. acetone or alkyl-aryl ketones, DMF or petrol ether different crystalline forms are observed revealing a certain degree of polymorphism of these particular sugar-S-(+)-ibuprofen complexes.

EXAMPLE 9

Synthesis Of S-(+)-2-(6-Methoxy-2-Naphthyl)-Propionic Acid

Very good chemical yields (80%) of this compound are obtained in high optical purity (95%) according to the routes outlined in Examples 4 and 5, especially when using Collman's reagent in the presence of carbon monoxide with subsequent hypochlorite oxidation.

Recrystallization of the raw material with mp 252-253° C. yields crystalline specimens having a melting point of 154° C. (lit mp 152-154° C.); $[\alpha]_D^{25} + 64.5°$ (C=1.08 CHCl$_3$), NMR (CHCl$_3$); 1.6 (D, 3H, CH—CH$_3$); 3.92 (S, 3H, OCH$_3$), 3.88 (g, 1H, CH) and 7-7.9 (m, 6H, aromatic).

MS resulted in the following spectra (FAB, glycerol matrix): m/z=23, $[M+H]^{30}$, 185 $[M-HCOOH+H]^{30}$, 323 $[M+6+H]^{30}$, 115 $[6+Na]^+$ and 229 $[m-H^-$ with 6=glycerol.

Measurements of the optical purity of this compound are accomplished by converting the carboxylic acid to the corresponding amide using S-(−)-methylbenzyl amine as described above, using HPLC-techniques which give the following results:

the chromatographic composition of the formed diastereoisomers are 3.6% R-2-(6-methoxy-2-naphthyl)-propionamide (6.15 min) and 96.4% S-2-(6-methoxy-2-naphthyl)-propionamide (6.95 min).

EXAMPLE 10

Synthesis Of S-(+)-2-(5-Bromo-6-Methoxy-2-Naphthyl)-Propionic Acid, As Methyl Ester After stereospecific reduction of the ketone as described in Examples 1 and 2 with (+)-(2S,3R)-4-dimethylamino-3-methyl-1-2-diphenyl 2 butanol and LiAlH$_4$ to the corresponding R-carbinol, subsequently converted to the R-halide and treatment with sodium tetracarbonyl ferrate-II in the presence of triphenylphosphine yields the corresponding carboxylic acid in a chemical yield of 75% having an optical purity of almost 95%. The melting point, mp, is determined to be 168° C.; $[\alpha]_D^{20}+42.7$ (0.8%) in chloroform. The methyl ester is easily obtained by reacting the carboxylic acid with diazo-methane, following evaporation of the solvent under reduced pressure, which gives the optically pure S-(+)-2-(5-bromo-6-methoxy-2-naphthyl)-propionic acid methylester.

Melting point, mp 96° C.; $[\alpha]_D^{20}+52.5$ (c=0.5, CHCl$_3$). The product is considered to be optically pure by $^1$H-MMR (200 MHz) analysis, which is carried out in CHCl$_3$ applying an optically active shifting agent as described above (EuIII-trix [3-heptafluoropropylhydroxy methylene)-d-camphorate].

EXAMPLE 11

Synthesis of R-(−)-2-(5-Bromo-6-Methoxy-2-Naphthyl)-Propionic Acid

Performing the reduction of the ketone with (−) 2,2 dihydroxy-1,1'-binaphthyl-LiAlH$_4$-ROH complex, as described in Example 2 in the presence of molecular sieves, yields an optically pure S-2-(5-bromo-6-methoxy-2-naphthyl)-hydroxy ethane (98%) in almost quantitative chemical yield. Following the route via nitrile with following oxidation to the corresponding carboxylic acid yields in almost 75% chemical yields of the optically pure R-(−)-2-(5-bromo-6-methoxy-2-naphthyl) propionic acid, having a melting point=168° C.; $[\alpha]_D^{20}-42.0$ (c=0.6%, chloroform).

EXAMPLE 12

Synthesis of 2-S-(+)-(4-Chlorphenyl)-3-Methyl-Butanoic Acid From 1-(4-Chlorphenyl)-3-Methylbutanone The ketone can be prepared from 3-methyl-butyryl chloride (128.6 g=1.07 moles) through Friedel-Craftsreaction with aluminium chloride (153.7 g=1.15 moles) in methylene chloride under the continuous addition of chlorbenzene (100 g=0.80 moles). The stereospecific reduction of this ketone with (+)-(2S,3R)-4-dimethylamino-3-methyl-1,2-diphenyl-2-butanol in the presence of LiAlH$_4$ is performed at 20° C. as described in Example 1. The R-carbinol which is 90% pure with respect to optical purity is converted to the corresponding R-halide with SOCl$_2$ and pyridine, subsequently treated with sodiumtetracarbonyl-ferrate-II in the presence of carbon monoxide as described in Example 5.

The obtained crude carboxylic acid is purified on DEAF-Sephadex-A50, applying a linear gradient at pH 7.9, ranging from 0.001M K$_2$HPO$_4$ to 0.01M K$_2$HPO$_4$ in a total volume of 1000 ml. The fraction containing optically active materials (+) are pooled, lyophilized and investigated for optical purity. The overall chemical yield is 71%, $[\alpha]_D^{20}+39.7$ (c 0 1%, chloroform).

EXAMPLE 13

The corresponding biphenyl and phenoxy-propionic acid derivatives can be prepared following the same procedures as outlined in the Examples 1-5. Below are listed some compounds which are prepared in accordance with the routes of Example 1-5, showing the optical activity and chemical yields.

S-(+)-2-(2-fluoro-4-biphenyl) propionic acid, $[\alpha]_D^{20}+44.7$, chemical yield 80%, S-(+)-2-(2-[4-(2-fluorophenoxy)phenyl]) propionic acid, having $[\alpha]_D^{20}+49$, chemical yield 70%, and S-(+)-2-(2-hydroxy-4-biphenyl)propionic acid, $[\alpha]_D^{20}+47$.

EXAMPLE 14

Preparation Of Solid Melts Of S-(+)Ibuprofen And Polyethylenglycol 1500

500 g of polyethylenglycol 1500 are melted in the absence of water in a container at 55° C. ±3° C., under continuous stirring. Solid 500 g S-(+)-ibuprofen is added under continuous stirring, also. It is possible to mix 500 g of polyethylenglycol 1500 with 500 g S-(+)-ibuprofen and melt the mixture in a container under stirring at 55° C. A clear, liquid melt is formed which is transparent when viewed at day light, when the liquid melt is cooled down to 40° C. This liquid (40° C.) can be filled in hard gelatin capsules easily in any dosage form one would like to have. After the appropiate filling the hard gelatin capsules are left at approximately 32° C., where a solid is being obtained which does not need to be sealed.

In order to accommodate fast solidifying of the liquid contents of the mixture, one can add some crystalline seeds of either S-(+)-ibuprofen or (R,S)-ibuprofen in order to increase the number of nucleation sites.

What is claimed is:

1. A process for forming a pharmaceutically active carboxylic acid in stereospecific form having the formula

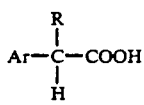

or a pharmaceutically acceptable salt thereof
wherein R is lower alkyl and
Ar is a monocyclic, polycyclic or orthocondensed polycyclic aromatic group having up to 12 carbons in the aromatic ring and which may be substituted or unsubstituted in the aromatic ring which comprises:

(a) reacting a carbonyl substrate of the formula:

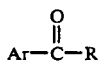

with an effective amount of a stereospecific reagent selected from the group consisting of (+)-4-dimethylamino-3-methyl-1,2-diphenyl-2-butanol and 2,2'-dihydroxy-1,1-binaphthyl in the presence of lithium aluminum hydride and in an organic solvent to form a R or S carbinol of the formula:

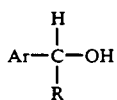

(b) reacting the product thereof with a halogenating agent to form the stereospecific R or S halide;
(c) reacting the halide with cyanide to form the corresponding nitrile with inversion; and
(d) hydrolyzing the nitrile to form the stereospecific carboxylic acid.

2. The process according to claim 1 wherein the carboxylic acid formed is in the S configuration.

3. The process according to claim 3 wherein the product is ibuprofen or naproxen.

4. The process according to claim 1 wherein the product is S-ibuprofen or S-naproxen.

5. The process in accordance with claim 1 wherein the halide is the R-halide.

6. The process in accordance with claim 5 in which the halide is in the R configuration having the formula

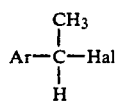

wherein Hal is Cl or Br.

7. The process in accordance with claim 1 in which the S-carbinol is reacted with SOCl$_2$ or SOBr$_2$ in a solvent consisting of pyridine and water.

8. The process according to claim 1 in which the R halide is formed by reacting the R-carbinol with cyanuric chloride, SOCl$_2$ or SOBr$_2$ in anhydrous solvent, wherein the R halide is in the R configuration having the formula

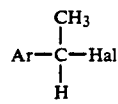

wherein Hal is Cl or Br.

9. The process according to claim 8 in which the solvent is pyridine or dioxane.

10. The process according to claim 1 in which the cyanide is alkali cyanide.

11. The process according to claim 10 in which the alkali cyanide is sodium cyanide or potassium cyanide.

12. The process according to claim 1 wherein the halide is the R-halide and the cyanide is alkali cyanide.

13. The process according to claim 1 wherein the product is hydrolyzed with acid.

14. The process according to claim 13 in which the product is hydrolyzed with aqueous hydroxide base containing about 6-8% H$_2$O$_2$.

15. The process according to claim 14 in which the base is sodium hydroxide.

16. The process according to claim 15 in which the R halide is reacted with potassium cyanide and the nitrile product thus formed is hydrolyzed with aqueous NaOH containing about 6-8% H$_2$O$_2$.

17. The process according to claim 15 wherein the R-halide is reacted with sodium cyanide and the nitrile product thus formed is hydrolyzed with aqueous NaOH containing about 6-8% H$_2$O$_2$.

18. A process for forming a pharmaceutically active carboxylic acid in stereospecific form having the formula

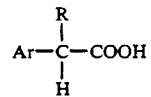

or a pharmaceutically acceptable salt thereof
wherein R is lower alkyl and
Ar is a monocyclic, polycyclic or othocondensed polycyclic aromatic group having up to 12 carbons in the aromatic ring and which may be substituted or unsubstituted in the aromatic ring which comprises:

(a) reacting a carbonyl substrate of the formula:

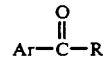

with an effective amount of (S)-(−)-1,1-diphenylprolinol in the presence of a complex between boron hydride and tetrahydrofuran in an organic solvent to form a R or S carbinol of the formula:

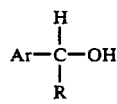

(b) reacting the product thereof with a halogenating agent to form the stereospecific R or S halide;
(c) reacting the halide with cyanide to form the corresponding nitrile with inversion; and
(d) hydrolyzing the nitrile to form the stereospecific carboxylic acid.

19. The process according to claim 18 in which R is methyl.

20. The process according to claim 1 in which molecular sieves are additionally present in step (a).

21. The process according to claim 20 in which the molecular sieves are 3Å or 4Å molecular sieves.

22. A process for preparing in the S configuration a compound of the formula:

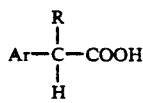

or a pharmaceutically acceptable salt thereof wherein
R is lower alkyl and
Ar is a monocyclic, polycyclic or orthocondensed polycyclic aromatic compound having up to 12 carbons in the aromatic ring and which may be substituted or unsubstituted in the aromatic ring which comprises (a) reacting a carbonyl substrate of the formula

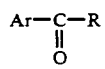

under effective conditions in an organic solvent with an effective amount of a reagent in the presence of lithium aluminum hydride, said reagent consisting of (+)-4-dimethylamino-3-methyl-1,2,diphenyl-2-butanol and 2,2'-dihydroxy-1,1-binaphthyl or an effective amount of (S)-(−)-1,1-diphenylprolinol in the presence of a complex between boron hydride and tetrahydrofuran to form a S carbinol of the formula

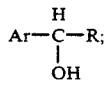

(b) reacting the carbinol with an effective amount of a halogenating agent to form the corresponding R-halide;

(c) reacting the R-halide with an effective amount of cyanide to form the S-nitrile; and (d) hydrolyzing the S-nitrile to form the S-carboxylic acid.

23. The process according to claim 22 wherein the reagent is (+)-4-dimethylamino-3-methyl-1,2-diphenyl-2-butanol or 2,2-dihydroxy-1,1-binaphthyl.

24. The process according to claim 23 wherein molecular sieves are additionally present.

25. The process according to claim 24 wherein the molecular sieves are 3Å or 4Å molecular sieves.

26. The process according to claim 22 in which R is methyl.

27. The process according to claim 22 in which Ar is 4-isobutylphenyl, 6-methoxy-2-naphthyl, 3-phenoxyphenyl, 2'-fluoro-4-diphenyl, 4'-fluoro-4-diphenyl, 5-chloro-6-methoxy-2-naphthyl, 5-bromo-6-methoxy-2-naphthyl, 4-chlorophenyl, 4-difluoromethoxyphenyl, 6-hydroxy-2-naphthyl or 5-bromo-6-hydroxy-2-naphthyl.

28. The process according to claim 22 wherein

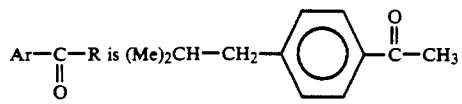

29. The process according to claim 22 wherein the reagent is (+)-4-dimethylamino-3-methyl-1,2-diphenyl-2-butanol and the process of step (a) is conducted at about −70° C.

30. The process according to claim 22 wherein Ar is

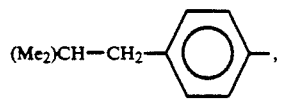

R is methyl, the reagent is (+)-4-dimethylamino-3-methyl-1,2-diphenyl-2-butanol and the reaction temperature of step (a) is about −70° C.

31. The process according to claim 22 wherein the reagent is 2,2'-dihydroxy-1,1-binaphthyl and the temperature of step (a) is approximately 20° C.

32. The process according to claim 22 wherein Ar is

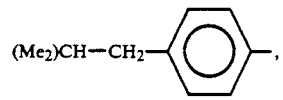

R is methyl, and the reagent is 2,2'-dihydroxy-1,1'-binaphthyl and the temperature of step (a) is approximately 20° C.

33. The process according to claim 22 wherein the R-halide has the formula

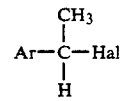

wherein Hal is chloride or bromide.

34. The process according to claim 22 in which the S carbinol is reacted with $SOCl_2$ or $SOBr_2$ in a solvent consisting of pyridine and water.

35. The process according to claim 22 in which the cyanide is alkali cyanide.

36. The process according to claim 33 wherein the alkali cyanide is sodium cyanide or potassium cyanide.

37. The process according to claim 22 wherein the S-nitrile is hydrolyzed with acid.

38. The process according to claim 22 in which the S-nitrile is hydrolyzed with aqueous hydroxide base containing about 6–8% $H_2O_2$.

39. The process according to claim 38 in which the base is sodium hydroxide.

40. A process for preparing in the R configuration a compound of the formula

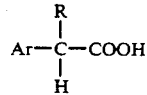

or a pharmaceutically effective salt thereof wherein
R is lower alkyl;
Ar is a monocyclic, polycyclic or orthocondensed polycyclic aromatic compound having up to 12 carbons in the aromatic ring and which may be unsubstituted or substituted in the aromatic ring which comprises (a) reacting a carbonyl substrate of the formula:

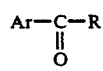

at effective temperature with an effective amount of a reagent in the presence of lithium aluminum hydride, said reagent consisting of (+)-4-dimethylamino-3-methyl-1,2-diphenyl-2-butanol and 2,2'-dihydroxy-1,1-binaphthyl or with an effective amount of (S)-(−)-1,1-diphenylprolinol in the presence of a complex between boron hydride and tetrahydrofuran to form a R carbinol of the formula:

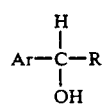

(b) reacting the carbinol with an effective amount of a halogenating agent to form the corresponding S-halide, (c) reacting the S-halide with an effective amount of cyanide to form the R-nitrile and (d) hydrolyzing the R-nitrile to form the R-carboxylic acid.

41. The process according to claim 40 wherein the reagent is (+)-4-dimethylamino-3-methyl-1,2-diphenyl-2-butanol or 2,2-dihydroxy-1,1-binaphthyl.

42. The process according to claim 41 wherein molecular sieves are additionally present.

43. The process according to claim 42 wherein the molecular sieves are 3Å or 4Å molecular sieves.

44. The process according to claim 40 in which R is methyl.

45. The process according to claim 40 in which Ar is 4-isobutylphenyl, 6-methoxy-2-methoxy-2-naphthyl, 3-phenoxyphenyl, 2'-fluoro-4-diphenyl, 4'-fluoro-4-diphenyl, 5-chloro-6-methoxy-2-naphthyl, 5-bromo-6-methoxy-2-naphthyl, 4-chlorophenyl, 4-difluoromethoxyphenyl, 6-hydroxy-2-naphthyl or 5-bromo-6-hydroxy-2-naphthyl.

46. The process according to claim 40 wherein

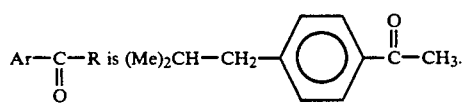

47. The process according to claim 40 wherein the temperature of step (a) is about 0° C. and the reagent is (+)-4-dimethylamino-3-methyl-1,2-diphenyl-2-butanol.

48. The process according to claim 40, wherein Ar is

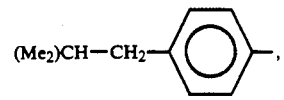

R is methyl, the reagent is (+)-4-dimethylamino-3-methyl-1,2-diphenyl-2-butanol and the reaction temperature of step (a) is about 0° C.

49. The process according to claim 40 wherein the R-halide has the formula

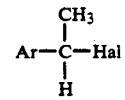

wherein Hal is chloride or bromide.

50. The process according to claim 40 in which the S carbinol is reacted with $SOCl_2$ or $SOBr_2$ in a solvent consisting of pyridine and water.

51. The process according to claim 40 in which the cyanide is alkali cyanide.

52. The process according to claim 51 wherein the alkali cyanide is sodium cyanide or potassium cyanide.

53. The process according to claim 40 wherein the R-nitrile is hydrolyzed with acid.

54. The process according to claim 40 in which the S-cyanide is hydrolyzed with aqueous hydroxide base containing about 6-8% $H_2O_2$.

55. The process according to claim 40 in which the base is sodium hydroxide.

56. The process according to claim 22 wherein step (a) comprises adding to and dissolving 3-methyl-1,2-diphenyl-2-butanol and $LiAlH_4$ an organic solvent, allowing said solution to stand at a temperature of about −70° C. to 0° C. for a time sufficient to form a microemulsion and subsequently adding said carbonyl substrate thereto.

57. The process according to claim 26 wherein the carbonyl substrate is 2-(4-isobutylphenyl)-methyl ketone or 1-[4-2-methylpropyl]phenyl ethanone.

58. The process according to claim 40 wherein step (a) comprises adding (+) 4-dimethyl amino-3-methyl-1,2-diphenyl-2-butanol and $LiAH_4$ to an organic solvent with stirring at temperatures ranging from 0° C. to −50° C. and before evolution of hydrogen, adding the carbonyl substrate thereto.

59. The process of claim 58 wherein the carbonyl substrate is added within ten minutes after the addition of the butanol and $LiAH_4$ to the organic solution.

60. The process according to claim 58 wherein the carbonyl reagent is 2-(4-isobutylphenyl) methyl ketone or 1-[4-2-methylpropyl]phenyl ethanone.

61. The process according to claim 1 wherein the carbinol formed in step (a) is the S-carbinol.

62. The process according to claim 22 in which the R-halide is reacted with potassium cyanide, and the nitrile product thus formed is hydrolyzed with acid.

63. The process according to claim 22 wherein the R-halide is reacted with sodium cyanide and the nitrile product thus formed is hydrolyzed with acid.

64. The process according to claim 1 in which the halogenating agent is thionyl bromide, thionyl chloride or cyanuric chloride.

65. The process according to claim 22 in which the halogenating agent is $SOCl_2$, $SOBr_2$ or cyanuric chloride.

66. The process according to claim 40 in which the halogenating agent is $SOCl_4$, $SOBr_2$ or cyanuric chloride.

* * * * *

UNITED STATES PATENT AND TRADEMARK OFFICE
CERTIFICATE OF CORRECTION

PATENT NO. : 5,266,723
DATED : November 30, 1993
INVENTOR(S) : Samir B. Hanna, et al.

It is certified that error appears in the above-identified patent and that said Letters Patent is hereby corrected as shown below:

In the Abstract, insert the following paragraph after the last line of the Abstract: --Moreover, a sterochemical synthesis of R or 2-(R)-aryl-alkanoic acids is disclosed, using the disclosed enantiomers of S- or R-substituted 2-carbinols of ethane via the corresponding nitriles, or applying sodiu-m cyanoferrate (II) in the presence of carbon monoxide--

On the Title Page, under "OTHER PUBLICATIONS", line 2: "Blaschle" should read --Blaschke--

On the Title Page, under "OTHER PUBLICATIONS", page 2, Column 2, line 8: "1089" should read --1989--, and line 10, "198092" should read --1980 92--

Column, line 26: "14313" should read --143138--
Column 3, line 26: "14313" should read --143138--
Column 11, line 56: "$C_6H_5$ " should read --$C_6H_5 \cdot$ "
Column 13, line 29: "molal" should read --molar--
Column 15, line 1: "$MW_{app}$" should read --$\overline{MW}_{app}$ --
Column 15, lines 4 & 5: "Rg" should read --$\underline{Rg}$--
Column 15, line 8: "$MW_{app}$" should read --$\overline{MW}_{app}$ --
Column 16, line 29: "R*OH.LiAlH " should read --R*OH•LiAlH --
Column 16, line 44: "R*OH.HCl" should read --R*OH•HCl --
Column 17, line 5: "R*OH.LiAlH$_4$" should read --R*OH LiAlH$_4$ --
Column 17, line 20: "Et$_2$o" should read --Et$_2$O --
Column 18, line 26: delete second occurrence of "be"
Column 19, line 24: "(Cll$_4$ )" should read --(Cll$_4$))--
Column 19, line 38: "[4-isobutylphenyl)" should read --[4-isobutylphenyl] --
Column 20, line 8: "DMF,DMSO" should read --DMF, DMSO--
Column 20, line 23: "dispered" should read --dispersed--
Column 20, line 58: "the" should read --The--
Column 21, line 19: "[M + H]$^{30}$" should read --[M + H]$^+$ -- and "[M-HCOOH + H]$^{30}$" should read --[M-HCOOH + H]$^+$ --

UNITED STATES PATENT AND TRADEMARK OFFICE
CERTIFICATE OF CORRECTION

PATENT NO. : 5,266,723

DATED : November 30, 1993

INVENTOR(S) : Samir B. Hanna, et al.

It is certified that error appears in the above-identified patent and that said Letters Patent is hereby corrected as shown below:

Column 21, line 20: "$[M + 6 + H]^{30}$" should read --$[M + 6 + H]^{+}$--
Column 21, line 20: "[m-H" should read --[M-H]] --
Column 21, line 53: " 'H-MMR" should read -- $^1$H--MMR --
Column 22, lines 13-14: "Craftsreaction" should read --Crafts-reaction--
Column 22, line 31: "0 1%" should read --0.1%--
Column 22, line 38: "Example" should read --Examples--
Column 23, line 44, Claim 3: "claim 3" should read --claim 1--
Column 27, line 15, Claim 40: "temperature" should read --temperatures--
Column 28, line 4, Claim 48: "$(Me_2)CH$" should read --$(Me_2)$-CH--
Column 28, line 34, Claim 56: before "an" insert --in--
Column 28, line 43, Claim 58: "$LiA H_4$ " should read --$LiAlH_4$ --
Column 28, line 49, Claim 59: "$LiAH_4$ " should read --$LiAlH_4$ --
Colum 28, line 65, Claim 66: "$SOCl_4$ " should read --$SOCl_2$ --

Signed and Sealed this

Fifteenth Day of April, 1997

Attest:

BRUCE LEHMAN

Attesting Officer     Commissioner of Patents and Trademarks